(12) United States Patent
Hong et al.

(10) Patent No.: US 8,980,570 B2
(45) Date of Patent: Mar. 17, 2015

(54) COMPOSITION FOR CANCER PROGNOSIS PREDICTION COMPRISING ANTI-TMAP/CKAP2 ANTIBODIES

(75) Inventors: Kyeong Man Hong, Goyang-si (KR); Chang Dae Bae, Suwon-si (KR); Joo Bae Park, Suwon-si (KR); Chang Ho Shin, Chungbuk (KR); Yong Book Choi, Goyang-si (KR)

(73) Assignees: National Cancer Center, Goyang-si (KR); Research and Business Foundation Sungyunkwan University, Goyang-si (KR)

( * ) Notice: Subject to any disclaimer, the term of this patent is extended or adjusted under 35 U.S.C. 154(b) by 0 days.

(21) Appl. No.: 13/577,126

(22) PCT Filed: Feb. 1, 2011

(86) PCT No.: PCT/KR2011/000691
§ 371 (c)(1),
(2), (4) Date: Oct. 22, 2012

(87) PCT Pub. No.: WO2011/096698
PCT Pub. Date: Aug. 11, 2011

(65) Prior Publication Data
US 2013/0045486 A1 Feb. 21, 2013

(30) Foreign Application Priority Data

Feb. 5, 2010 (KR) .......................... 10-2010-0011126
Aug. 20, 2010 (KR) .......................... 10-2010-0081081

(51) Int. Cl.
*G01N 33/53* (2006.01)
*C07K 16/30* (2006.01)
*G01N 33/574* (2006.01)

(52) U.S. Cl.
CPC .............. *C07K 16/30* (2013.01); *G01N 33/574* (2013.01)
USPC .......................................... 435/7.23; 435/7.1

(58) Field of Classification Search
None
See application file for complete search history.

(56) References Cited

FOREIGN PATENT DOCUMENTS

WO 03093794 A2 11/2003

OTHER PUBLICATIONS

Hong et al, Exp Mol Med. 2008, 40(4): 377-386.*
Bae et al, J Cancer Oncol 129:621-630, 2003.*
Jeon BBRC, 348:222-228, 2006.*
Hong Ku et al. Cdk1-Cyclin B 1-mediated Phosphorylation of Tumor-associated Microtubule-associated Protein/Cytoskeleton-associated Protein 2 in Mitosis. J. Biological Chemistry. 2009, vol. 284, No. 24, pp. 16501-16512.
Hong Ku et al. Transient phosphorylation of tumor associated microtubule associated protein (TMAP)/cytoskeleton associated protein 2 (CKAP2) at Thr-596 during early phases of mitosis. Experimental and Molecular Medicine. 2008, vol. 4, No. 4, pp. 377-386.
Ross et al., The HER-2/neu Gene and Protein in Breast Cancer 2003: Biomarker and TArget of Therapy, 2003, pp. 307-325, The Oncologist, US.
Hong, Cdk1-Cyclin B1-mediated Phosphorylation of Tumor-associated Microtubule-associated Protein/Cytoskeleton-associated Protein 2 in Mitosis, journal, 2009, p. 16501-16512, vol. 284 (24), J Biological Chemistry, US.

* cited by examiner

*Primary Examiner* — Lei Yao
(74) *Attorney, Agent, or Firm* — Benjamin Aaron Adler

(57) ABSTRACT

The present invention relates to an antibody which specifically binds to TMAP (tumor associated microtubule associated protein)/CKAP2 (cytoskeleton associated protein 2) or a fragment thereof, and a method for identifying the presence or absence of mitosis and a method for diagnosing cancer prognosis using the same. More specifically, the present invention relates to a composition for diagnosing cancer prognosis comprising an anti-TMAP/CKAP2 antibody or an antigen-binding site thereof, a method for detecting TMAP/CKAP2 using the composition, an anti-TMAP/CKAP2 antibody for diagnosing cancer prognosis, a method for providing information for diagnosing cancer prognosis using the composition, a method for screening a cancer therapeutic agent comprising the step of determining changes in the level of TMAP/CKAP2 antigen-antibody reaction by the treatment of a candidate substance, and a composition for determining cell-division cycles using the composition.

5 Claims, 13 Drawing Sheets

FIG. 2

Human TMAP/CKAP2 HeavyG-C

Nucleotide sequence (SEQ ID NO.37)

<u>CTAGTCGACATGGGTTGGGTGTGGACCTTGCCATTCCTCCTGTCAGGAACTGCAGGT</u>
GTCCATTGCCAGGCTCAGCTGCAGCAGTCTGGACCTGAGCTGGTGAAGCCTGGGGCTTTA
GTGAAGATATCCTGCAAGGCTTCTGGTTATATCTTCACAAACTACGATATAAACTGGGTG
AAGCAGAGGCCTGGACAGGGTCTTGAGTGGATTGGATTGATTTATCCTGGAGATGGCAGT
ATTAAGTACAATGAGAAATTCAAGGGCAAGGCCACACTGACTGCAGACAAATCCTCCAGC
ACAGCCTACATGCAGCTCAGCAGCCAGACTTCTGAGAACTCTGCAGTCTATTTCTGTGCA
AGATCCGGCCCGTATTACTTTGACTATCTGGGGCCAAGGCACCACTCTCACAGtTCTCGC underlined: primer region
bold: start codon Deduced amino acid sequence (SEQ ID NO.45)

```
                                                              CDR1(SEQ ID NO.38)
LVDMGWVWTLPFLLSGTAGVHCQAQLQQSGPELVKPGALVKISCKASGYIF NYDIN WVK
QRPGQGLEWIG LIYPGDGSIKYNEKFKG KATLTADKSSSTAYMQLSSQTSENSAVYFCAR
 SGPYYFDYL GPRHHSHSSR         CDR2(SEQ ID NO.39)
CDR3(SEQ ID NO.40)
```

FIG. 3

Human TMAP/CKAP2 Light k-E & k-F were same sequence
Nucleotide sequence (SEQ ID NO.41)

ACTAGTCGACATGAGTGTGCYCACTCAGGTCCTGGGGTTGCTTATGTTCTGGATCTC
TGGAGTCAGTGGGGATATTGTGATAACCCAGGATGAACTCTCCAATCCTGTCATTTTTGG
AGAATCAGTTTCCATCTCCTGCAGGTCTAGTAAGAGTCTCCTATATAAGGATGGGAAGAC
ATACTTGAATTGGTATCTGCAGAGACCAGGACAATCTCCTCAGCTCCTGATCTATTTGAT
GTCCACCCGTGCATCAGGAGTCTCAGACCGGTTTAGTGGCAGTGGGTCAGGAACAGATTT
CACCCTGGAAATCAGTAGAGTGAAGGCTGAGGATGTGGGTGTGTATTACTGCCAACAAGT
TGTAGAGTATCCATTCACGTTCGGCTCGGGGACAAAATGGAAA underlined: primer region
bold: start codon Deduced amino acid sequence (SEQ ID NO.46)

CDR1(SEQ ID NO.42)

LVDMSVXTQVLGLLMFWISGVSGDIVITQDELSNPVIFGESVSISC**RSSKSLLYKDGKTY
LNWYLQRPGQSPQLLIYLMSTRASGVSDRFSGSGSGTDFTLEISRVKAEDVGVYYCQQVV
EYPFT**FGSGTKWK          CDR2(SEQ ID NO.43)
CDR3 (SEQ ID NO.44)

COMPOSITION FOR CANCER PROGNOSIS PREDICTION COMPRISING ANTI-TMAP/CKAP2 ANTIBODIES

BACKGROUND OF THE INVENTION

1. Field of the Invention

The present invention relates to an antibody which specifically binds to TMAP (tumor associated microtubule associated protein)/CKAP2 (cytoskeleton associated protein 2) or a fragment thereof; and a method for identifying the presence or absence of mitosis and a method for diagnosing cancer prognosis using the same. More specifically, the present invention relates to a composition for diagnosing cancer prognosis comprising an anti-TMAP/CKAP2 antibody or an antigen-binding site thereof, a method for detecting TMAP/CKAP2 using the composition, an anti-TMAP/CKAP2 antibody for diagnosing cancer prognosis, a method for providing information for diagnosing cancer prognosis using the composition, a method for screening a cancer therapeutic agent comprising the step of determining changes in the level of TMAP/CKAP2 antigen-antibody reaction by the treatment of a candidate substance, and a composition for determining cell-division cycles using the composition.

2. Description of the Related Art

In Korea, cancer (malignant neoplasm) is responsible for the death of 62,887 persons per, which corresponds to 25.5% (23.6% for men and 20.5% for women) of the total death toll of 246,515 persons (death rate 512 per hundred thousands of the population) in 2002, ranking it first amongst the causes of death. Lung cancer, gastric cancer, hepatic cancer, colorectal cancer, and pancreatic cancer are in decreasing order the cancers with the highest mortality rates, these five cancers accounting for around 70% of total cancer deaths. Lung cancer, gastric cancer, hepatic cancer and colorectal cancer are the leading causes of cancer death in males, the four cancers account for 28, 147 deaths in that period (around 70% of all cancer deaths (40,177)). For women, 13, 630 deaths, which were around 60% of the total cancer deaths in that period (22,710), were caused by the five cancers of gastric cancer, lung cancer, hepatic cancer, colon cancer and pancreatic cancer.

There are many different types of cancers currently known, reaching several dozen, and cancers are generally classified according to the tissue of origin. Cancer cells grow very rapidly, and invade nearby tissue, leading to metastasis, and thus can directly threaten life. The types of cancer include cerebrospinal tumor, head and neck cancer, lung cancer, breast cancer, thymoma, esophagus cancer, pancreatic cancer, colon cancer, hepatic cancer, biliary tract cancer, etc. Cancer can be also divided further by classification according to pathogenesis or morphology.

Among them, breast cancer is the most common cancer in women other than skin cancer. Even though improved detection methods, mass screening, and advances in treatment over the last decade have significantly improved the outlook for woman diagnosed with breast cancer, many women still-suffer from breast cancer. Approximately 20% of women diagnosed with early-stage breast cancer have a poor ten-year outcome and will suffer disease recurrence, metastasis or death within this time period. On the contrary, the remaining 80% of breast cancer patients diagnosed at an early stage have a good ten-year prognosis. Like this, even though diagnosed with the same stage, patients diagnosed with early-stage breast cancer have different prognosis. Thus, there is an urgent need for evaluation methods capable of distinguishing between them.

Prognostic indicators provide tumor size, nodal status and histological grade, as well as some information regarding prognosis, and suggest response to particular treatments. For example, determination of estrogen (ER) and progesterone (PR) steroid hormone receptor status has become a routine procedure in assessment of breast cancer patients. Tumors that are hormone receptor positive are more likely to respond to hormone therapy and also typically grow less aggressively, thereby resulting in a better prognosis for patients with ER+/PR+ tumors.

Meanwhile, over expression of human epidermal growth factor receptor 2 (HER-2) and a transmembrane tyrosine kinase receptor protein has been correlated with poor breast cancer prognosis (Ross et al. (2003) The Oncologist: 307-325). Currently, Her2/neu expression levels in breast tumors are used to predict response to the anti-Her-2/neu antibody therapeutic agent, trastuzumab (Herceptin; Genentech). In addition, Ki-67 is a non-histone nuclear protein that is expressed during the G1 through M phases of the cell cycle. Studies have shown that Ki-67 overexpression also correlates with poor breast cancer prognosis.

Although current prognostic criteria and molecular markers provide some guidance in predicting patient outcome and selecting appropriate course of treatment, there is still a limit in predicting breast cancer prognosis. Accordingly, there is an urgent need to develop a method for effectively predicting prognosis or to develop an indicator capable of diagnosing them.

With regard to other cancers, lung cancer was a rare disease in the 19th century, but the increased incidence of lung cancer in the 20th century was first attributed to cigarette smoking. In Korea, the incidence of lung cancer is also rapidly increasing. Furthermore, since lung cancer is more fatal than other types of cancer, it remains the leading cause of cancer-related death, even though its incidence does not rank first.

The underlying mechanism of cancer development remains poorly defined, but it is generally understood, that cancer is the result of uncontrolled growth of cells due to genetic mutations that disrupt the normal regulation of cell proliferation. According to stages of cancer development, early cancer stage is defined as tumor invasion confined to the mucosa, which has a considerably better prognosis in most cancers. Thus, it is assumed that early diagnosis and treatment of cancer contribute to the reduction of the mortality rate and cancer treatment cost. However, at an early stage, cancer rarely causes symptoms, if any, such as digestive disorders or abdominal discomfort. Thus, people often ignore these symptoms, leading to an increase in the mortality rate.

To date, cancer diagnosis has been made by physical examination. For example, gastrointestinal X-ray examination methods may be broadly classified into the double contrast method, the compression method, the mucosa relief method, etc, and endoscopic examination is advantageous in that it directly visualizes the internal organ to find small lesions that are not detected by X-ray, and permits biopsy of suspicious lesions, whereby the diagnosis rate is increased. However, endoscopic examination has problems that, there is a chance of contamination, and patients have to experience significant discomfort during the procedure.

In addition, surgical resection of the lesion is the best method that can be conducted for the treatment of cancer, and thus is the only curative treatment currently available for cancer. For complete cure, surgical resection with a maximum surgical margin is generally recommended, but the extent of surgery may be determined in consideration of postoperative complications. However, when cancer spreads to other organs, radical surgery is not possible, and thus other treatments such as chemotherapy are adopted. Anticancer agents currently available serve to temporarily alleviate symptoms or to prevent recurrence and prolong survival time after surgical resection. However, there is a limitation in complete treatment of cancer, and chemotherapy causes severe side effects, and also imposes economic: burden on the patients.

Therefore, it is important to develop a method capable of diagnosing cancer with high sensitivity and specificity, prior to treatment, and the method should be established to diagnose cancer at an early stage. Furthermore, there is a need of personalized diagnostics and therapy based on prediction of cancer prognosis. Until now, there has been no significant progress in a molecular diagnostic technology of determining cancer occurrence by specific detection of a lesion at an early stage, and it is within bounds to say that there is no diagnostic method for particular cancers.

Meanwhile, cell proliferation and growth are essential for cancer development, and most cancer cells undergo abnormal mitotic cell division. A type of cell cycle, normal mitotic cell division is the series of events leading to division of a single cell into two cells, and consists of the G1 phase (preparation step for cell proliferation), S phase (Interphase) (DNA replication), G2 phase (later stage of DNA synthesis) and M phase (Mitotic phase). The major checkpoints that, ensure the fidelity of cell division lie in between the G1 and 3 phase and G2 and M phase, and promote progression of normal cells into the next stage and apoptosis of abnormal cells. In addition, normal cells often leave G1 phase and enter a quiescent G0 phase at the restriction point if there is a shortage of growth factors or nutrients. In particular, M phase is the shortest and the most dramatic phase since at this time the replicated genome is segregated to the opposite pole of the cell and the two daughter cells are generated. The series of events lead to the division of a cell into two daughter cells, and thus this process underlies growth and development in all living organisms. When cells are divided in M phase, they should enter the next phase through the growth in G1 phase. However, cancer cells lose the ability to undergo apoptosis due to DMA damage, and thus cannot progress to the next stage at the checkpoint and stay in M phase. Consequently, excessive rate or cell division leads to a larger number of cells. That is, cancer cells disrupt the normal cell division mechanisms and continuously proliferate in M phase. Therefore, it is expected that a marker capable of detecting abnormal cell cycles can be effectively used, for the development of cancer diagnostic and therapeutic agents.

On the basis of this background, the present inventors have made many efforts to develop a marker capable of detecting cell cycles for the diagnosis of cancer. As a result, they found that detection of TMAP/CKAP2 expression and its level can be used for the examination of specific cell division, cycles and for the diagnosis of cancer, and it can be also used as an index for predicting overall survival and disease-free survival of breast cancer patients, thereby completing the present invention.

SUMMARY OF THE INVENTION

An object of the present invention is to provide a composition for diagnosing cancer prognosis, comprising an anti-TMAP/CKAP2 (Tumor associated microtubule associated protein/cytoskeleton associated protein 2) antibody or an antigen-binding site thereof.

Another object of the present invention is to provide an antibody for diagnosing cancer prognosis, which specifically binds to TMAP/CKAP2.

Still another object of the present invention is to provide a kit for diagnosing cancer prognosis, comprising the anti-TMAP/CKAP2 antibody or the antigen-binding site thereof.

Still another object of the present invention is to provide a method for detecting TMAP/CKAP2 in an individual having cancer using the composition comprising the antibody or the antigen-binding site thereof.

Still another object of the present invention is to provide a method for providing information for diagnosing cancer prognosis, comprising the steps of (a) treating a control sample separated from an individual known to have good prognosis and a sample separated from an individual suspected of having cancer with the anti-TMAP/CKAP2 antibody or the antigen-binding site thereof; (b) comparing antigen-antibody reaction levels of step (a); and (c) determining the individual suspected of having cancer as a cancer patient having a poor prognosis when the antigen-antibody reaction level of the sample separated from the corresponding individual is higher than that of the control sample in step (b).

Still another object of the present invention is to provide a method, for screening a cancer therapeutic agent comprising the steps of (a) determining the TMAP/CKAP2 antigen-antibody reaction level in cancer cells using the composition comprising the anti-TMAP/CKAP2 antibody or the antigen-binding site thereof; (b) treating the cells with a candidate substance; and (c) examining whether the antigen-antibody reaction level after treatment of the candidate substance of step (b) is lower than that of step (a).

Still another object of the present invention is to provide a composition for determining cell division cycle comprising the anti-TMAP/CKAP2 antibody or the antigen-binding site thereof.

BRIEF DESCRIPTION OF THE DRAWINGS

FIG. 2 shows the nucleotide sequence and amino acid sequence of heavy chain region of human TMAP/CKAP2 antibody.

FIG. 3 shows the nucleotide sequence and amino acid sequence of light chain, region of human. TMAP/CKAP2 antibody.

DETAILED DESCRIPTION OF THE PREFERRED EMBODIMENTS

Figure 1:
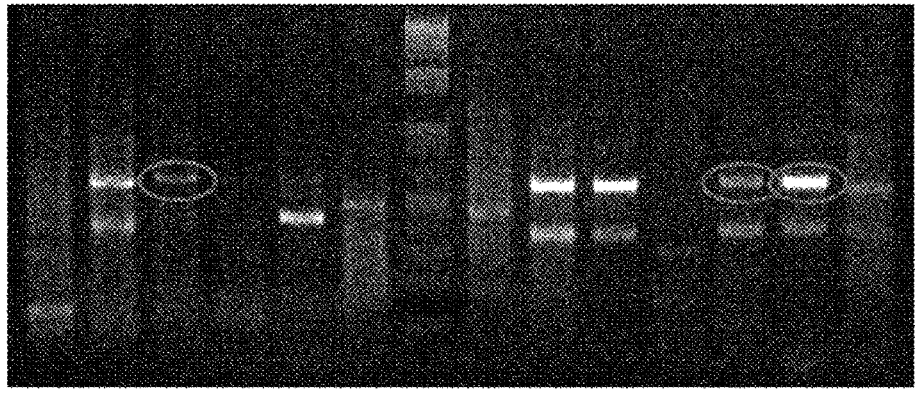
FIG. 1 shows the result of electrophoresis of PCR products on a 2% agarose gel after PCR using immunoglobulin-specific primer sets.
Figure 4:
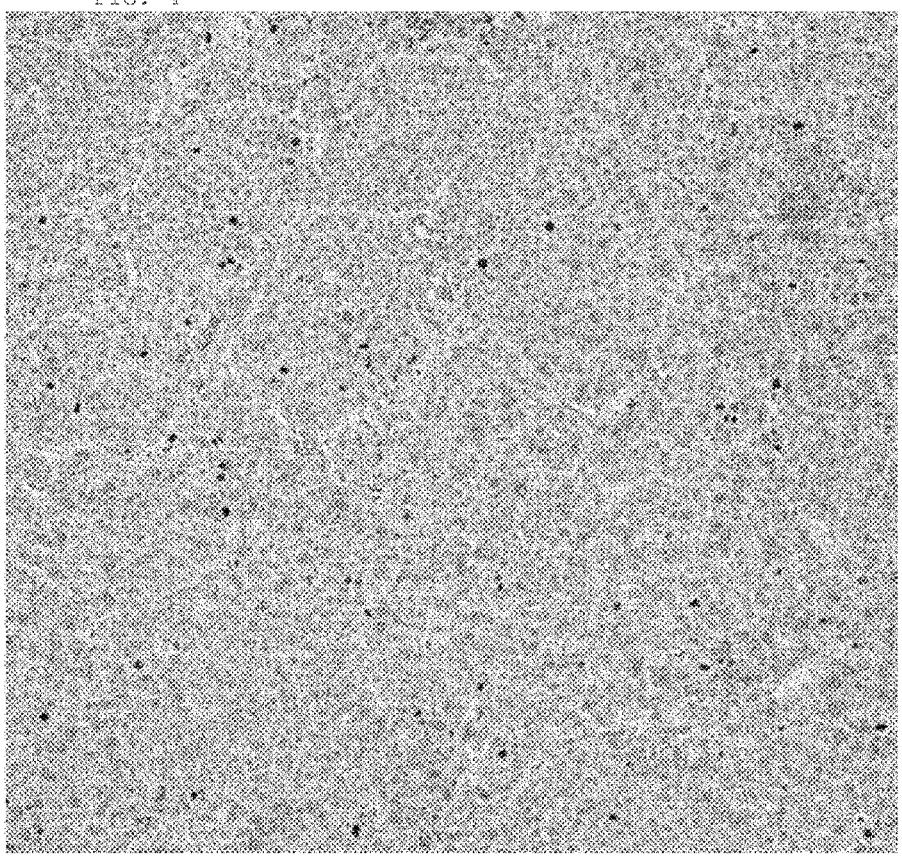
FIG. 4 shows the result of immunohistochemistry (×100) of hepatic cancer tissues using anti-TMAP/CKAP2 antibody, in which brown or black-colored cells represent, staining of chromosome with antibodies, and most of the cells undergoing division were stained.
Figure 5:
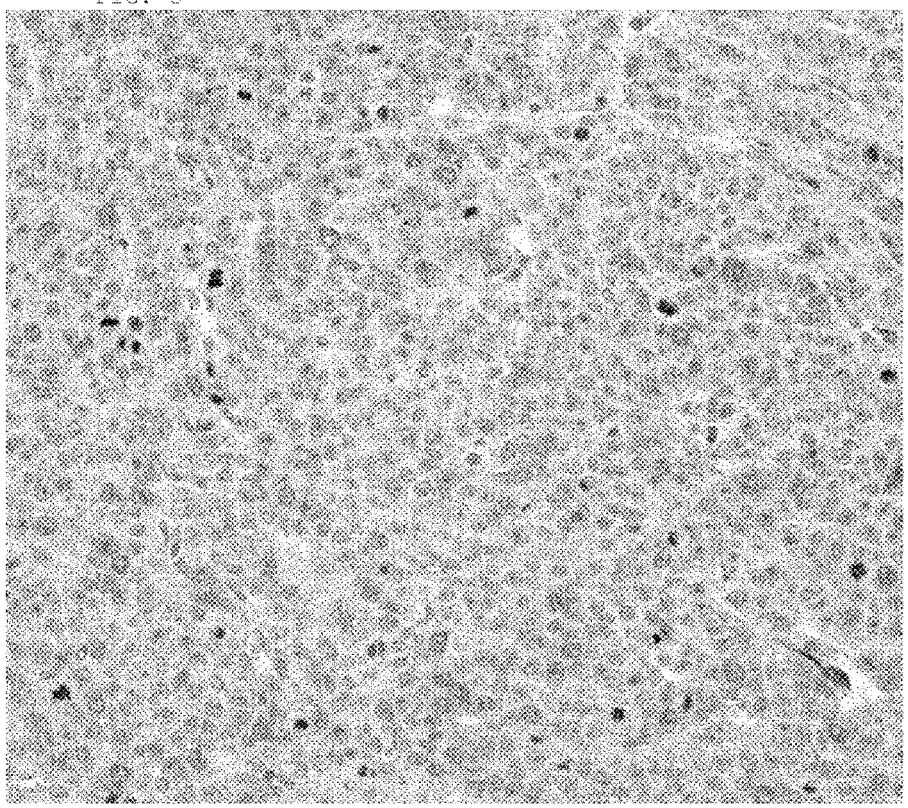
FIG. 5 snows the result of immunohistochemistry (×200) of hepatic cancer tissues using anti-TMAP/CKAP2 antibody (higher magnification than FIG. 4), in which cells showing cytoplasmic staining did not show nuclear staining, and the cells just entering mitotic phase were observed.
Figure 6:
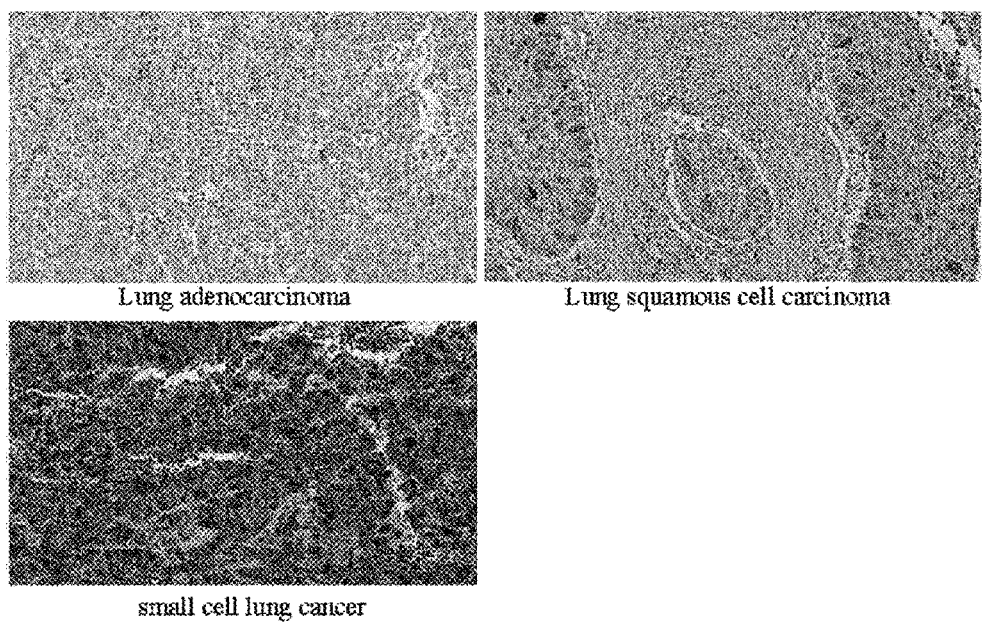
FIG. 6 shows the result of immunohistochemistry of various lung cancer tissues using anti-TMAP/CKAP2 antibody, in which squamous cell carcinoma snowed higher expression than adenocarcinoma, and small cell lung cancer showed much higher expression than non-small cell carcinoma.
Figure 7:
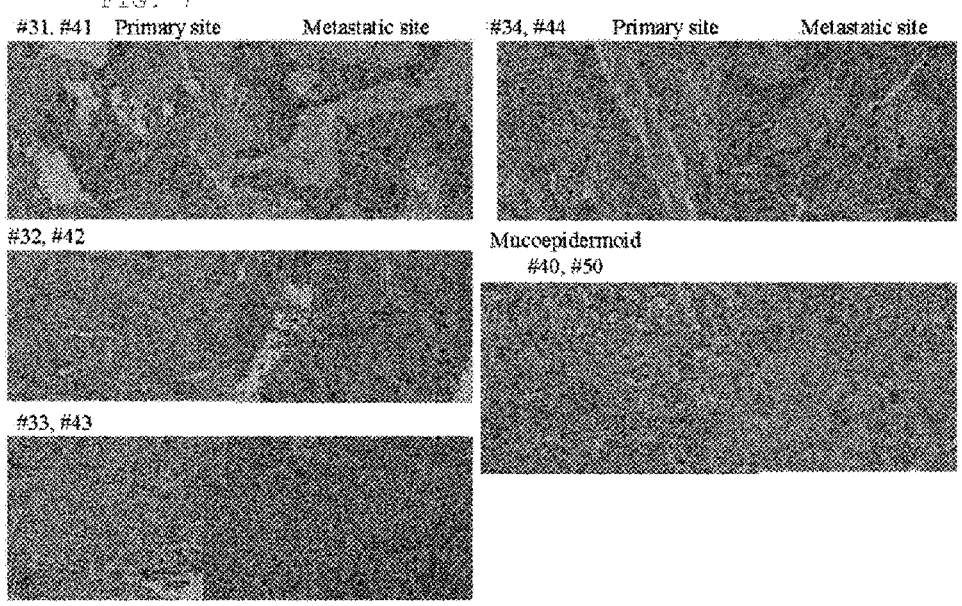
FIG. 7 shows the result of immunohistochemistry of primary and metastatic lung cancer tissues using anti-TMAP/CKAP2 antibody, in which metastatic lung cancer tissue showed higher TMAP/CKAP2 expression than primary lung cancer tissue, the predominant expression was observed, in squamous cell carcinoma among non-small cell lung cancers, and the increased expression as in metastatic lung cancer tissues was not observed in adenocarcinoma.

In one aspect to achieve the above objects, the present invention relates to a composition for diagnosing cancer prognosis comprising an anti-TMAP/CKAP2 (Tumor associated microtubule associated protein/cytoskeleton associated protein 2) antibody or an antigen-binding site thereof.

The term "diagnosis", as used herein, means confirmation of a pathological state or characteristic. With respect to the objects of the present invention, the diagnosis is to confirm, the incidence of cancer as well, as recurrence following cancer treatment, metastatic spread, and drug reactivity and resistance. Preferably, when the anti-TMAP/CKAP2 antibody of the present invention is used, the TMAP/CKAP2 expression level in a sample of an individual can be determined to examine the cancer incidence of the corresponding individual, and to predict the prognosis of the corresponding individual. Further, the term "prognosis", as used herein, refers to the prediction of the likelihood of liver cancer-attributable death or progression, including recurrence, metastatic spread, and drug resistance of neoplastic diseases such as cancer. With respect to the objects of the present invention, the "prognosis" thus means to predict the prognosis of breast cancer, gastrointestinal stromal tumor, hepatic cancer, squamous cell carcinoma, non-small cell carcinoma, or small cell carcinoma, and preferably prediction of the disease-free survival or overall survival of breast cancer patients.

As used herein, the term, "disease-free survival" means probability of survival without, cancer recurrence after operation, and the term "overall survival" means probability of survival regardless of cancer recurrence.

The term "diagnostic marker, marker for diagnosis, or diagnosis marker", as used herein, means a material capable of distinguishing cancer cells from normal cells, and may include an organic biomolecule such as a polypeptide, a nucleic acid (e.g., mRNA etc.), a lipid, a glycolipid, a glycoprotein, and a sugar (monosaccharide, disaccharide, oligosaccharide etc.), which is expressed at a higher or lower level in cancer cells having a poor prognosis, as compared to its level, in normal cells or cancer cells having a good prognosis. Preferably, the diagnostic marker for cancer of the present invention, is TMAP/CKAP2.

As used herein, the term "TMAP/CKAP2" is an abbreviation of tumor associated microtubule associated protein/cytoskeleton associated protein 2, and also known as LB1 and se20-10. Preferably, the composition of the present invention is used to examine occurrence and prognosis of cancer in the corresponding individual by detection of TMAP/CKAP2. Preferably, the composition of the present invention can be used for the diagnosis and prognosis of hepatic cancer, lung cancer, breast cancer, thyroid cancer, testicular cancer, myelodysplasia, oral cancer, mycosis fungoides, acute myeloid leukemia, acute lymphoblastic leukemia, basal cell carcinoma, epithelial ovarian cancer, ovarian germ cell tumors, brain tumor, pituitary adenoma, multiple myeloma, gallbladder cancer, biliary tract cancer, colorectal cancer, chronic myeloid leukemia, retinoblastoma, choroidal, melanoma, bladder cancer, parathyroid cancer, non-small cell lung cancer, small cell lung cancer, pediatric brain tumor, pediatric lymphoma, vulvar cancer, cancer of unknown primary site, gastric lymphoma, gastric cancer, gastric carcinoid, tumor, gastrointestinal stromal tumor, Wilms tumor, penis cancer, pharyngeal cancer, gestational trophoblastic disease, cervical cancer, endometrial, cancer, uterine sarcoma, prostate cancer, metastatic brain tumor, rectal carcinoid tumor, vaginal, cancer, spinal cord, cancer, acoustic neuroma, pancreatic cancer, salivary gland, cancer, tonsillar cancer, squamous cell carcinoma, adenocarcinoma, large-cell carcinoma, skin cancer and larynx cancer, preferably, for the diagnosis and prognosis of metastatic cancers of the above cancers which are in active cell division, more preferably, for the diagnosis or prognosis of hepatic cancer or lung cancer, and much more preferably, for the prognosis of breast, cancer or gastrointestinal stromal tumor (GIST) of which prognosis is determined by mitotic activity. Most preferably, it can be used for predicting the disease-free survival or the overall survival of breast cancer patients.

In order to examine the diagnostic and prognostic effects of the composition of the present, invention, the present inventors performed immunohistochemical staining of human tumor tissues and different normal tissues using anti-TMAP/CKAP2 antibodies prepared, by the present inventors. The results showed that the number of stained cells was much higher in tumor tissues than normal tissues and TMAP/CKAP2 expression was hardly observed in most cells of normal tissues. In addition, they first demonstrated that TMAP/CKAP2 expression is highly associated with the overall survival and disease-free survival of breast cancer patients, which were examined, by 4 different analytic methods, chromosome permillage analysis, total permillage analysis, field chromosome count analysis, and field total-count analysis. The results snowed that higher TMAP/CKAP2 expression groups had lower disease-free survival and overall survival. In particular, the composition of the present invention binds with and stained, the chromosome and spindle fibers of cells in mitosis, thereby specifically detecting the active proliferation site resulting from abnormal cell division. That is, the composition of the present invention distinguishes the mitotic region by cancer occurrence and development from the surrounding stroma, and thus it is possible to detect the specific site and division stage.

Figure 8:
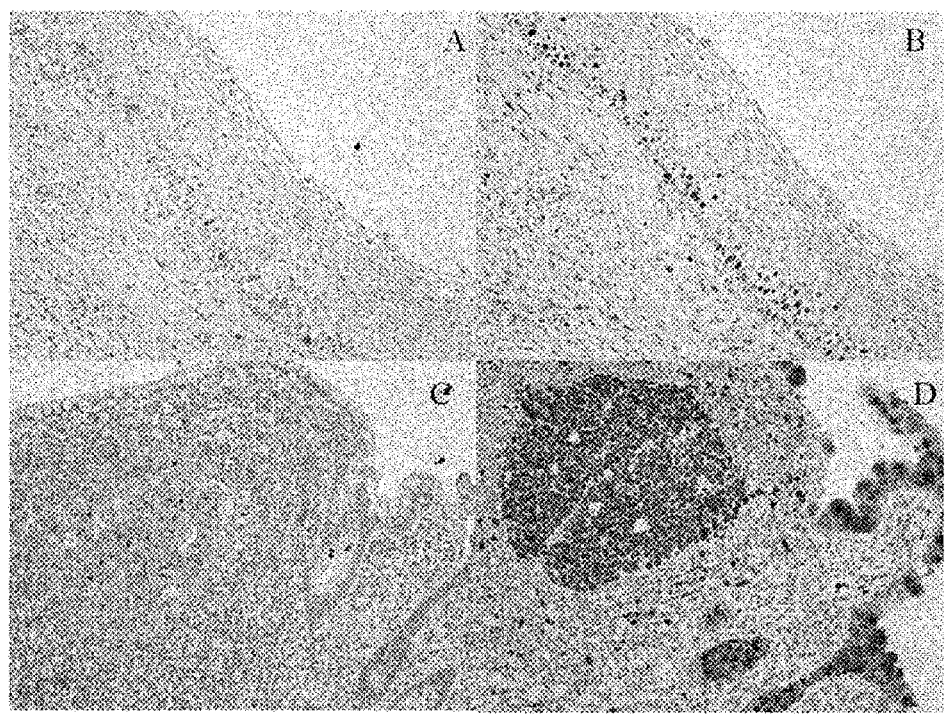
FIG. 8 shows the result of immunohistochemistry of normal tissues using anti-TMAP/CKAP2 antibody and anti-Ki67 antibody. Immunohistochemistry of the cervical tissues was performed using anti-TMAP/CKAP2 antibody (A) and anti-Ki67 antibody (B), in which the staining of two antibodies was observed only in cervical epithelial cells of the fundus known to undergo division, and the number of cells stained with anti-TMAP/CKAP2 antibody was lower than that of anti-Ki67 antibody, suggesting that TMAP/CKAP2 is expressed for a shorter period of mitosis. Immunohistochemistry of the actively dividing LF (lymphoid follicle) tissues was performed using anti-TMAP/CKAP2 antibody (C) and anti-Ki67 antibody (D), in which the number of cells stained with anti-TMAP/CKAP2 antibody was lower than that of anti-Ki67 antibody.
Figure 9:
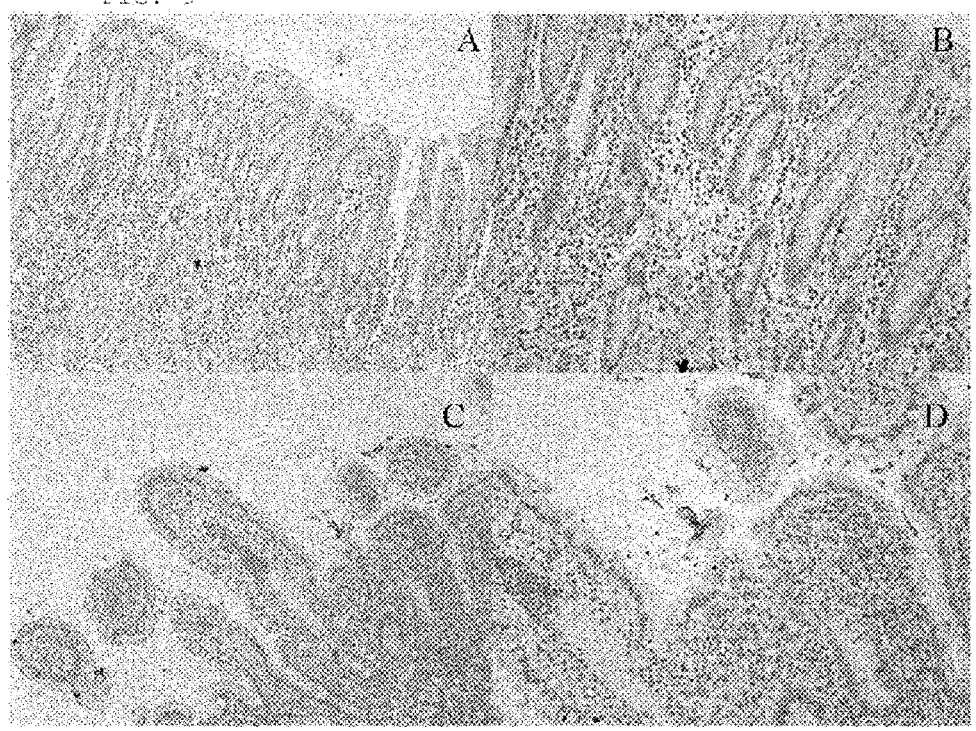
FIG. 9 shows the result of immunohistochemistry of gastric and colon tissues using anti-TMAP/CKAP2 antibody, in which staining of gastric and colon tissues with anti-TMAP/CKAP2 antibody was observed in the crypt cells known to undergo cell division, and FIG. 9A (×100) and FIG. 9B (×200) show gastric tissues and FIG. 9C (×100) and FIG. 9D (×200) show colon tissues.
Figure 10:
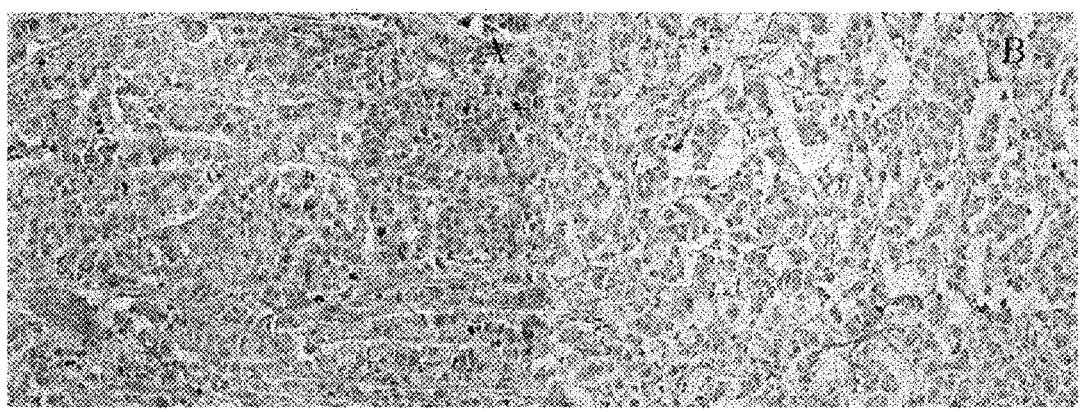
FIG. 10 shows the result of immunohistochemistry of breast cancer tissues using anti-TMAP/CKAP2 antibody. A large number of stained cells were observed in one of the breast cancer tissues (A) and only a small number of stained, cells were observed in the other breast cancer tissues (B), and this difference is closely associated with division degree of cancer cells. Chromosome or its surrounding structure stained with anti-TMAP/CKAP2 antibody indicates that cells are in mitotic phase, and a relatively weak staining indicates that cells are in the G2 to M phase transition. Cells having stained chromosome or surrounding structure can be used, as an important mitotic activity index, and a ratio of cells in the G2 phase to cells in the M phase reflects the status of G2/M checkpoint, implying a relationship with reactivity of anticancer agent.
Figure 11:
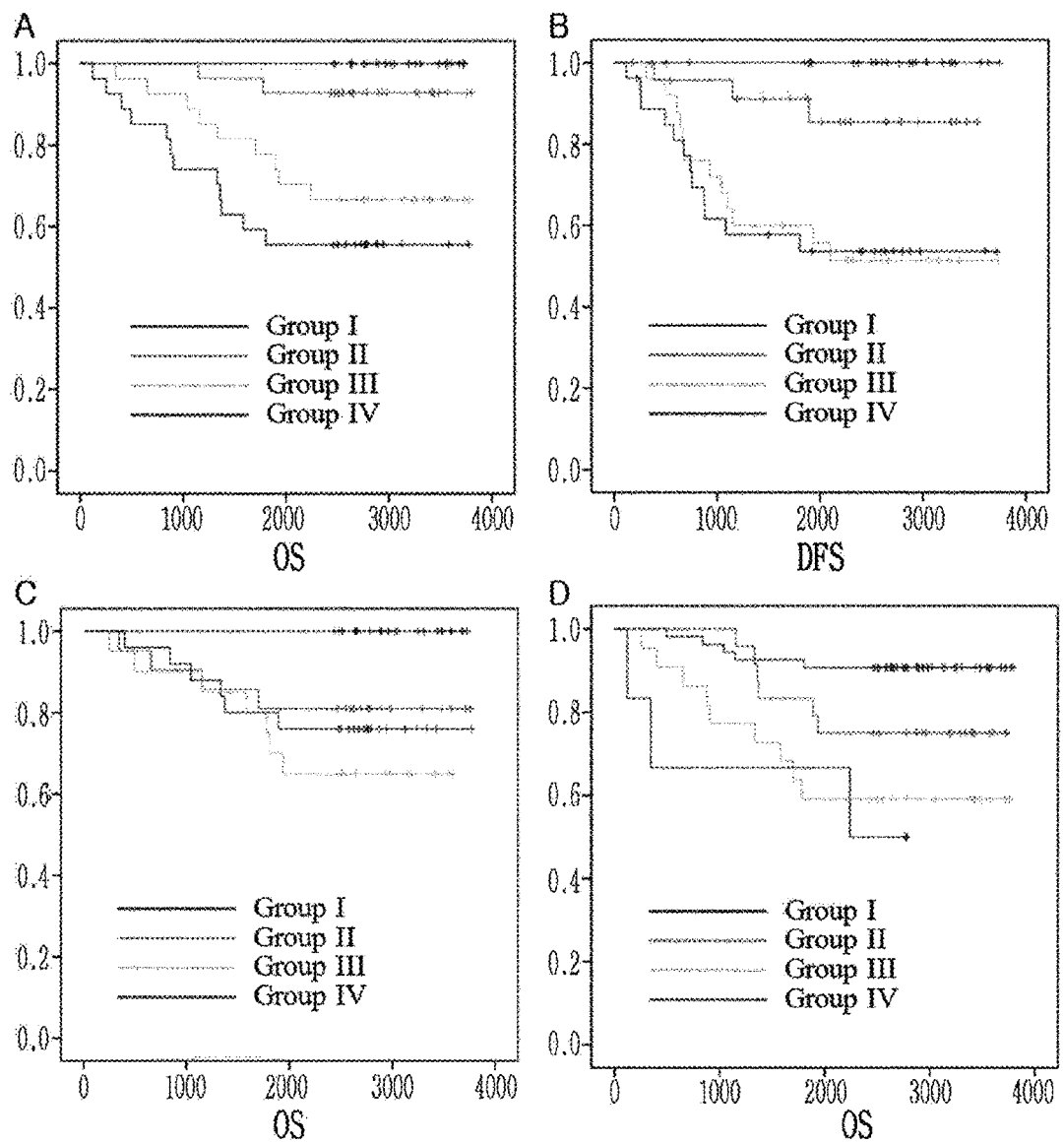
FIG. 11 shows Kaplan-Meier plots of overall survival and disease free survival according to TMAP/CKAP2 or Ki-67 expression level in breast cancer patients. Groups 2, 3 and 4 showed, a higher chromosome permillage of TMAP/CKAP2 positive cells and lower overall survival (A) and disease-free survival (B) than Group 1 showing a low TMAP/CKAP2 expression. In (C), Groups 2, 3 and 4 having a higher percentage of nuclear Ki-67 positive cells showed lower overall, survival than Group 1 having a lower percentage. (D) is a Kaplan-Meier plot of the overall survival, according to N stage, suggesting that TMAP/CKAP2 expression is a better predictor of overall survival than N stage known to have the highest predictive value for breast cancer prognosis. X-axis; overall survival after surgery, Y-axis; survival, probability.
Figure 12:
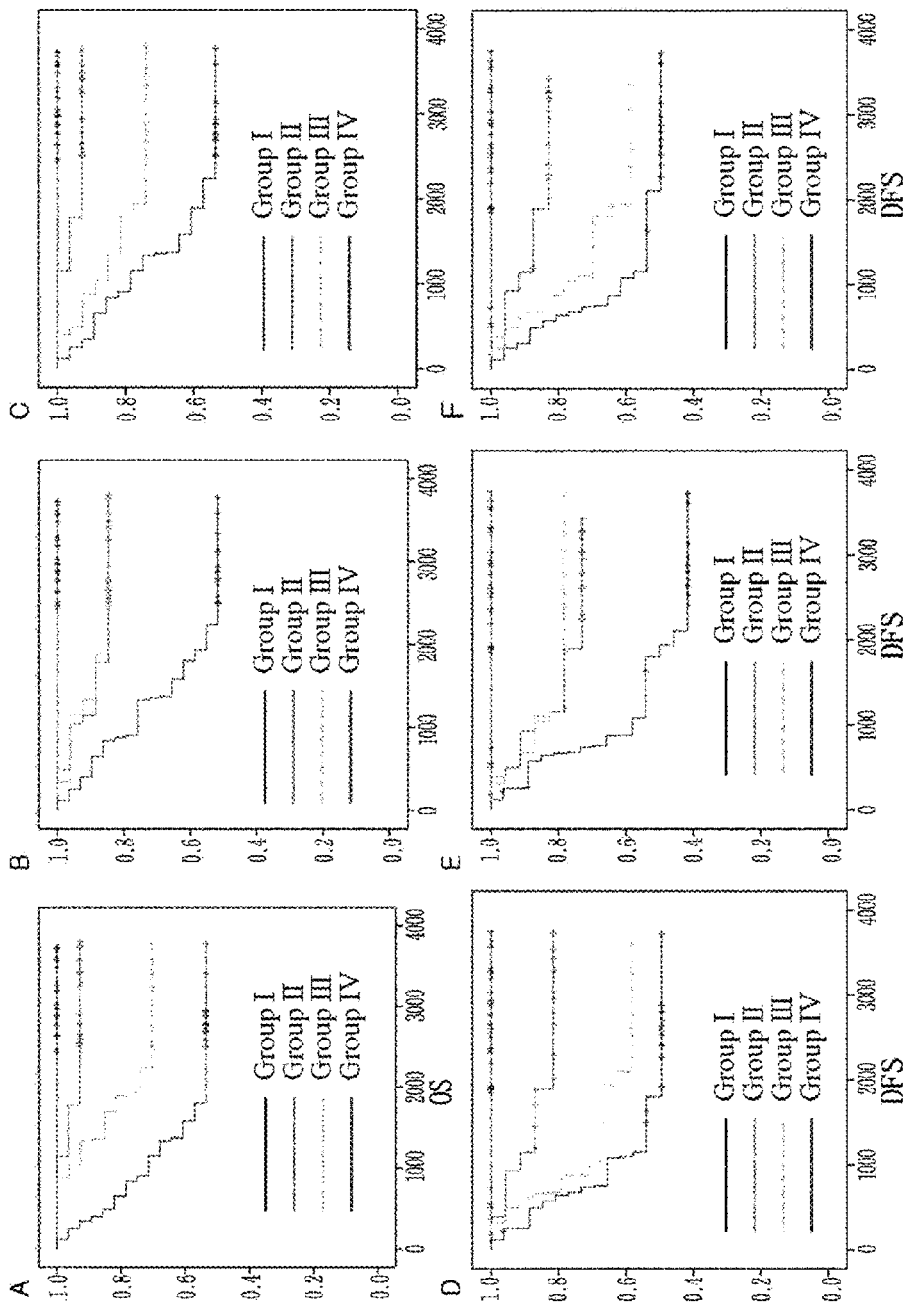
FIG. 12 shows Kaplan-Meier plots of overall survival (OS) and disease free survival (DFS) according to TMAP/CKAP2 expression level in breast, cancer patients. In accordance with field chromosome count (A and B), field total count (B and B) or total permillage (C and F) analysis, Kaplan-Meier plots of overall survival (A-C) and disease-free survival (D-F) were compared, between Groups 2, 3 and 4, and Group 1 showing the lowest expression level, indicating that as the TMAP/CKAP2 expression level is higher, breast cancer patients have lower overall survival and disease-free survival.
Figure 13:
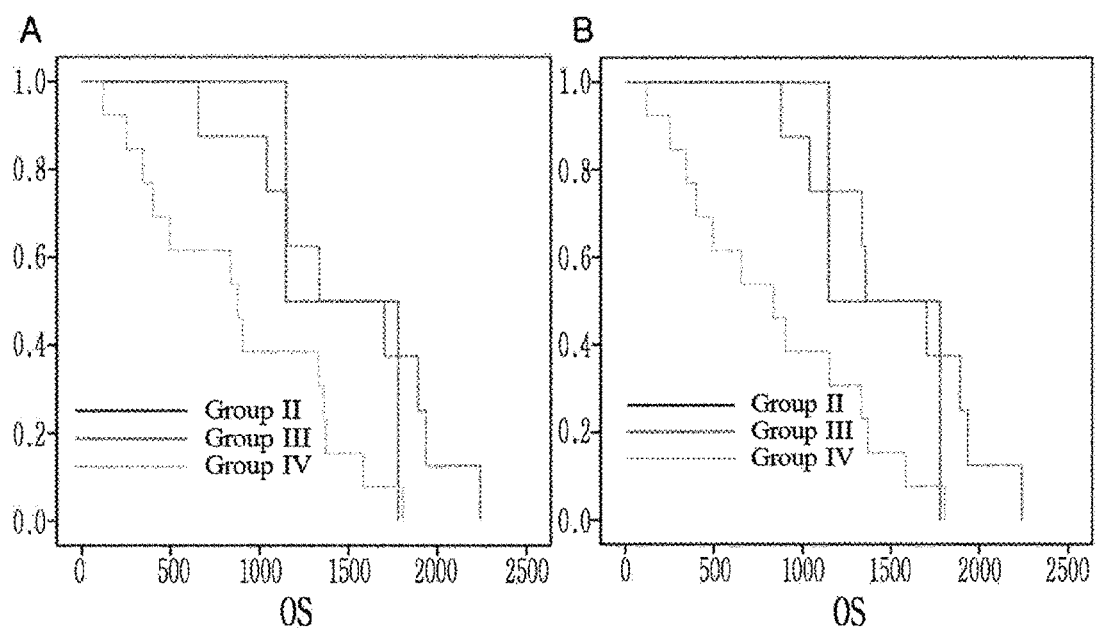
FIG. 13 shows Kaplan-Meier plots of overall survival of patients died of breast cancer, in which the patients of Group 4 showed, much lower overall survival than, the patients of Group 3. (A) chromosome permillage analysis (p=0.026); (B) total permillage analysis (p=0.013).

A relationship between TMAP/CKAP2 and B cell lymphoma, cutaneous T cell lymphoma, or breast cancer cell line has been partially known, but there have been no reports of its antibody for the diagnosis and treatment of cancer. Also, there has been no report of its use in the prognosis of cancer. In addition, there have been no reports of its use in the diagnosis of hepatic cancer and lung cancer, and small cell lung cancer, and as a means to distinguish small cell lung cancer from non-small cell lung cancer. With regard to breast cancer or gastrointestinal stromal tumor, the present inventors demonstrated, that prognosis of patients having the cancer caused, by proliferation resulting from cancer cell division can be predicted. Therefore, the present inventors directly prepared anti-TMAP/CKAP2 antibodies, and first identified its possibility for cancer diagnosis, and furthermore, its use for diagnosis and prognosis of cancer. They also demonstrated that it can be used as a prognostic marker for predicting the disease-free survival or the overall survival of breast cancer patients. More preferably, the composition of the present invention can be used for the diagnosis and prognosis of hepatic cancer and lung cancer, and more preferably, for the prognosis of breast cancer or gastrointestinal stromal tumor (GIST) of which prognosis is determined by mitotic activity. Most, preferably, the composition of the present invention can be used as a prognostic marker for predicting the disease-free survival or the overall survival of breast cancer patients. In the preferred embodiment of the present invention, the results of staining breast cancer tissues using the composition of the present invention showed that actively dividing breast cancer cells were specifically stained. Meanwhile, as compared to Ki-67 antibody that is known as a marker of cell division to predict the prognosis of breast cancer, the composition of the present invention was used to achieve specific staining of tissue undergoing cell division (FIG. 8). In one preferred, embodiment of the present invention, the composition of the present invention was used to analyze the overall survival and the disease-free survival of breast cancer patients after cancer resection. The results showed that higher TMAP/CKAP2 expression groups had lower disease-free survival and overall survival (FIGS. 11 to 13).

Breast cancer is a tumor mass originating from the breast, tissue, and most, commonly from the ducts or the lobules. The risk factors are, but not clearly defined, estrogen, age, birth experience, alcohol, and family history. The 5-year survival rate of breast cancer is nearly 100% for stage 0, and less than 20% for stage 4, and surgical resection, chemotherapy, radiation therapy, and antihormone therapy are commonly used for the treatment. It has been reported that the prognosis of breast cancer vary depending on the stage. In many cases, however, patients have different prognosis even at the same stage. Thus, there is an urgent need of a specific marker for the prognosis of breast, cancer.

Meanwhile, gastrointestinal stromal tumor (GIST) is the most common mesenchymal tumor of the gastrointestinal tract, and is known to be caused by a mutation of Kit gene or PDGFRA gene. Patients with GIST have dysphagia and gastrointestinal, hemorrhage, and a liver metastasis. It is also important to predict the prognosis of GIST. However, even though prediction of prognosis is greatly affected by proliferation degree of cancer cells, a specific prognostic marker is not identified yet, and thus there are still difficulties in the prognosis.

Actually, even though patients diagnosed with early-stage breast cancer are treated, with the same therapy, 20% of the patients have poor prognosis and die of recurrence or metastasis within 10 years. Therefore, effective diagnostic methods are required, for accurate prognosis, and the prognosis of breast cancer can be achieved by detection of mitotic activity. However, there has been, no significant progress in the development of a means for examining whether cancer cells actively proliferate or cell division actively occurs, apart from cancer development. The composition of the present invention provides a means for diagnosing the prognosis of breast cancer or GIST with accuracy. In detail, the composition of the present invention is administered, into target cells to examine cell division, and activity.

One of the most important prognostic factors of breast cancer or GIST is degree of cell division, which can be determined by using a mitotic activity index. As the mitotic activity index, the conventional method is to count the number of cells in the mitotic phase under a microscope after H&E staining of cancer tissues. However, this method has disadvantages of requirement of much time and subjective opinions of pathologists. Thus, there is much deviation between individuals. On the basis of this background, the present inventors have made many efforts to develop a method, for identifying cancer cells in the mitotic phase. As a result, they first demonstrated, that anti-TMAP/CKAP2 antibody can be used to easily distinguish between normal and cancer cells in the mitotic phase by immunohistochemistry of different human tissues and cancer tissues using anti-TMAP/CKAP2 antibody.

It is advantageous in that, the anti-TMAP/CKAP2 antibody can be used to easily identify cells in the mitotic phase by staining the chromosome or its surrounding structure, which makes it possible to provide an objective and rapid prognostic method of breast cancer or GIST. Many efforts and attempts have been made to identify cells in the mitotic phase using anti-Hi-67 antibody. Expression of Ki-67 is not restricted to the mitotic phase, and it is observed, in the cells through the late G1, S, G2 and M phases. Thus, a large number of cells are stained, and thus it has a limit as a mitotic activity index. However, the anti-TMAP/CKAP2 antibody of the present invention is able to specifically identify the chromosome or its surrounding structure in mitotic phase, and thus it is very advantageous in the identification of cells in mitotic phase. The composition comprising the anti-TMAP/CKAP2 antibody of the present, invention is also frequently found in the cytoplasm. It is assumed that these cells are in the G2 phase before mitotic entry. A ratio of cells in the G2 phase to cells in the M phase reflects the status of G2/M checkpoint, thereby providing important, information on prognosis of cancer patients or resistance and reactivity of anticancer agent. The composition of the present invention is the first composition capable of analyzing G2 and M phase distributions, and thus can be effectively used in the studies of anticancer agents and cancer prognosis.

Furthermore the TMAP/CKAP2 of the present invention is highly associated with the disease-free survival and the overall survival of breast cancer patients. That, is, as TMAP/CKAP2 expression is higher, the disease-free survival and the overall survival become lower. Therefore, survival and/or probability of breast patients can be predicted after treatment of particular therapeutic agents and/or cancer resection, and/or chemotherapy for a predetermined period without recurrence. The composition of the present, invention can be clinically used to determine therapy suitable for any particular patients. The prognostic composition of the present invention can be used to predict whether patients respond, favorably to specific therapies such as specific therapeutic agents or combinations thereof, surgical intervention, and chemotherapy, or whether patients survive for a long period of time after treatment. In one preferred embodiment of the present invention, overall survival was compared between TMAP/CKAP2 and Ki-67, which is the known index for cell division and proliferation. As a result, TMAP/CKAP2 was highly associated with overall survival (FIGS. 11A to 11C), suggesting that TMAP/CKAP2 can be used as a strong prognostic marker for predicting the disease-free survival and the overall survival of breast cancer patients.

Meanwhile, the composition of the present, invention shows sensitivity and specificity to small cell lung cancer in addition to breast cancer or GIST, and thus it was confirmed that the composition of the present invention can be used, for the diagnosis of small cell lung cancer, furthermore, used to distinguish small cell lung cancer from other cancers.

Lung cancer is largely divided into small cell lung cancer and non-small cell lung cancer, and non-small cell lung cancer is further divided into adenocarcinoma, squamous cell carcinoma, and large-cell carcinoma. Small cell lung cancer is classified as lung cancer by the location of cancer cells, but considered distinct from other types of lung cancer in terms of clinical outcome, therapy and prognosis.

Unlike non-small cell lung cancer, small cell lung cancer usually disseminated at diagnosis and is therefore not amenable to cure with surgery. It rapidly grows and early spread to distant sites, and shows exquisite sensitivity to chemotherapy or radiation. Small, cell lung cancer exhibits aggressive behavior, and frequently spread to other organs, opposite lung, and mediastinum, through lymphatic vessel or blood circulation. It was reported that small cell lung cancer primarily arises in the lining of the airway (in the bronchus or bronchiole). Small cell lung cancer is usually characterized by a grey-white large mass and arises in peribronchial locations, and most, often spreads to the brain, the liver, the bone, the lung, the adrenal glands, and the kidney.

Meanwhile, non-small cell lung cancer, as described above, is further classified into squamous cell carcinoma, adenocarcinoma and large-cell, carcinoma. Squamous cell carcinoma, tends to originate in the central airways, and frequently occurs in men, and is closely related to smoking. Squamous cell carcinoma causes central airway obstruction as a result of its endoluminal growth. On the contrary, adenocarcinoma commonly occurs in the peripheral lung, and in women or non-smokers. Even with a small size, the metastasis is frequently observed, and its incidence is currently growing. Lastly, large-cell carcinoma commonly occurs near the surface of the lung (in the peripheral lung), and approximately half of the cases occur in a large bronchus, and accounts for approximately 4 to 10% of all lung cancers. It generally has a large cell size, and tends to grow and metastasize rapidly, and thus carries a worse prognosis than other non-small cell lung cancers.

The cancer diagnostic marker comprising the anti-TMAP/CKAP2 antibody or the antigen-binding site thereof is highly expressed in various types of lung cancer, and thus can be used, as a diagnostic marker for most lung cancers. It was also confirmed, that the cancer diagnostic marker can be effectively utilized in the detection of lung cancers, in particular, small cell lung cancer. These characteristics of the present invention make it possible to diagnose small cell lung cancer as well as cancer including lung cancer and hepatic cancer, and to detect proliferation of cancer cells. Thus, it can be used to predict cancer prognosis. Furthermore, the present inventors demonstrated that the composition of the present invention can be effectively used, to distinguish between small cell lung cancer and non-small cell lung cancer, between which distinction cannot be easily made by the known methods. In detail, the present inventors performed, immunohistochemistry of lung cancer tissues to examine the diagnostic and detection accuracy of the present invention. According to the results, 1) there were differences in the TMAP/CKAP2 expression between different types of lung cancers, in particular, 2) higher expression was observed in squamous cell carcinoma than in adenocarcinoma, and 3) the composition of the present invention showed a high specific reactivity to small cell lung cancer, and practically, a strong TMAP/CKAP2 staining was observed in small cell, lung cancer cells. These results indicate that the composition is very useful as a diagnostic composition for the small, cell lung cancer because there is a difference in clinical outcome, prognosis, and treatment between small cell lung cancer and non-small cell lung cancer as described above, and furthermore, the composition of the present invention, can be used as an alternative or an additional diagnostic method when distinction between small cell lung cancer and non-small cell lung cancer cannot be easily made by other detection methods or diagnostic methods.

The composition of the present invention may include the anti-TMAP/CKAP2 antibody or the fragment thereof. The antibody of the present invention includes an immunoglobulin molecule immunologically reactive with a particular antigen, and includes both polyclonal and monoclonal antibodies. The term "monoclonal antibody", also a known term, refers to an antibody molecule obtained from a population of substantially homogeneous antibodies, and is highly specific, being directed against a single antigenic site. In contrast to polyclonal antibody which includes different antibodies directed against different epitopes, each monoclonal antibody is typically directed, against a single epitope on the antigen. Monoclonal, antibodies provide the benefit, of improving the selectivity and specificity to diagnostic and analytic techniques that utilize antigen-antibody complexes. Another benefit is that such monoclonal, antibodies are contamination-free as they are produced, through hybridoma cultivation.

It will be apparent to those skilled in the art that the monoclonal antibody according to the present invention can be converted into a chimeric antibody, at humanized antibody, and a human monoclonal antibody, of which immunogenicity is reduced, for applications in human bodies. The chimeric antibody is produced, by recombination of a variable region of the monoclonal antibody of the present invention and a constant region of a human antibody, the humanized antibody is produced by implanting complementarity determining regions (CDRs), which directly bind to an antigen, in a variable region of the monoclonal antibody of the present invention, or specificity determining residues (SDRs), which, are involved in antigen, binding specificity among the complementarity determining regions, into a human antibody.

The humanized antibody can be easily produced from the monoclonal antibody of the present invention using a well known method that includes the steps of replacing a heavy-chain variable region, or a light-chain variable region among the variable regions of the monoclonal antibody of the present, invention with a heavy-chain variable region or a light-chain variable region of a human antibody, then replacing a mouse heavy-chain variable region, or a mouse light-chain variable region from the resulting hybrid (mouse heavy cha in/human light-chain, or mouse light-chain/human heavy-chain) antibody having antigen-binding capacity, selecting a complete human antibody variable region having antigen-binding capacity, and linking it with the constant region of the human antibody. It is a matter of fact that these variants are encompassed by the present invention. Subsequently, the chimeric antibody, the humanized antibody, and the human monoclonal antibody can be produced in animal cells using a well known method.

Further, as long as the monoclonal antibody of the present invention has the binding property as described above, it can be a fragment thereof. That is, the antibody of the present invention is a complete form having a full length of two heavy-chains and two light-chains, as well, as a functional fragment, of the antibody molecule, and thus it can be used, for cancer treatment and diagnosis. Here, the phrase "the functional fragment of the antibody molecule" means a fragment containing at least antigen-binding capacity, and may include Fab, F(ab'), F(ab')$_2$, and Fv.

The monoclonal antibody of the present invention can be produced by a known preparation method of monoclonal antibody, for example, a fusion method well known in the art (Kohler et al., European Journal of Immunology 6; 511-519). This method is similar to the conventional hybridoma preparation method, but monoclonal antibodies can be obtained from a transgenic mouse with human immunoglobulin loci after inactivation of mouse immunoglobulin gene.

The monoclonal antibody can be also prepared by a phage display technique which is a technique of selecting antibody clones against a specific antigen by expressing a human antibody library on the surface of bacteriophage in a form of antibody fragment (Fab, ScRv), but the antibody preparation method of the present invention is not limited to the above methods.

Typically, an immunoglobulin has a heavy and light chain. Each heavy and light chain contains a constant region and a variable region, (the regions are also known as "domains"). Light and heavy chain variable regions contain three hypervariable regions, also called "complementarity-determining regions" (hereinafter, referred to as "CDRs"), and four "framework" regions. The CDRs are primarily responsible for binding to an epitope of an antigen. The CDRs of each chain are typically referred to as CDR1, CDR2, and CDR3, numbered sequentially starting from the N terminus, and are also typically identified by the chain in which the particular CDR is located.

The antibody of the present invention includes any antibody without limitation as long as it is able to specifically bind to TMAP/CKAP2 for predicting the cancer-prognosis, preferably, an antibody that comprises a heavy chain variable region comprising heavy chain CDR1 represented by SEQ ID NO. 38; heavy chain CDR2 represented by SEQ ID NO. 39; and heavy chain CDR3 represented by SEQ ID NO, 40 and a light chain variable region comprising light chain CDR1 represented by SEQ ID NO. 42; light chain CDR2 represented by SEQ ID NO, 43; and light chain CDR3 represented by SEQ ID NO. 44, and more preferably, an antibody that comprises a heavy chain amino acid sequence represented by SEQ ID NO. 45 and a light chain amino acid sequence represented by SEQ ID NO. 46.

In another aspect, the present invention relates to an antibody for diagnosing cancer prognosis, which specifically binds to TMAP/CKAP2. The antibody of the present invention includes an immunoglobulin molecule immunologically reactive with a particular antigen, and includes both polyclonal and monoclonal antibodies.

Description of the antibody is the same as described above.

The antibody of the present invention includes any antibody without limitation as long as it is able to specifically bind to TMAP/CKAP2 for diagnosing the cancer prognosis, preferably, an antibody that comprises a heavy chain variable region comprising heavy chain CDR1 represented, by SEQ ID NO, 38; heavy chain CDR2 represented by SEQ ID NO, 39; and heavy chain CDR3 represented by SEQ ID NO, 40 and a light chain variable region comprising light chain CDR1 represented by SEQ ID NO. 42; light chain CDR2 represented by SEQ ID NO. 43; and light chain CDR3 represented by SEQ ID NO. 44, and more preferably, an antibody that comprises a heavy chain amino acid sequence represented by SEQ ID NO, 45 and a light chain amino acid sequence represented by SEQ ID NO. 46.

In one preferred embodiment of the present invention, human TMAP/CKAP2 monoclonal antibody hybridomas were produced, and the sequences of positive clones were analyzed. As a result, it was found to have heavy chain and light chain regions having the DNA sequences of SEQ ID NOs. 37 and 41 (FIGS. 2 and 3).

In still another aspect, the present invention relates to a kit for diagnosing cancer prognosis, comprising the anti-TMAP/CKAP2 antibody or the antigen-binding site thereof. TMAP/CKAP2 and the available antibody or antigen-binding site thereof are the same as described above, and it is apparent that the kit can be prepared in a kit form typically used in the art by including the composition of the present invention as a component. With respect to the objects of the present, invention, cancers of which prognosis can be predicted by the anti-TMAP/CKAP2 antibody or the antigen-binding site thereof include any cancer described above without limitation, and preferably, the kit is a kit for predicting the prognosis of breast cancer, which is characterized by predicting the disease-free survival or the overall survival of breast cancer patients.

In still another aspect, the present invention relates to a method for detecting TMAP/CKAP2 in an individual having cancer by using the composition comprising the anti-TMAP/CKAP2 antibody or the antigen-binding site thereof.

As described below, the composition of the present invention can be used to detect TMAP/CKAP2 expressed in cells in the mitotic phase, and furthermore, the composition can be used to detect TMAP/CKAP2 in cancer patients, preferably, in an individual having lung cancer or hepatic cancer, more preferably, in an individual having small cell lung cancer, much more preferably, in an individual of which prognosis is diagnosed by determining cell division of cancer such, as breast cancer and GIST, and most preferably, in a breast cancer patient for diagnosing the disease-free survival or the overall survival.

In still another aspect, the present invention relates to a method for providing information for diagnosing cancer prognosis, comprising the steps of (a) treating a control sample separated from an individual known to have good prognosis and a sample separated from an individual suspected of having cancer with the anti-TMAP/CKAP2 antibody or the antigen-binding site thereof; (b) comparing antigen-antibody reaction levels of step (a); and (c) determining the individual suspected of having cancer as a cancer patient having a poor prognosis when the antigen-antibody reaction level of the sample separated from the corresponding individual is higher than that of the control sample in step (b).

In the present invention, preferably, the sample is treated with the anti-TMAP/CKAP2 antibody, and the reactivity was compared to examine the prognosis of the individual having cancer. This method can be also achieved by comparing the antigen-antibody reaction of a control individual known to have good prognosis. Preferably, it means to predict the disease-free survival or the overall survival of breast cancer patients.

The term "individual known to have good prognosis", as used herein, means an individual having no metastasis, recurrence, or death after cancer occurrence. The term, "the sample of an individual suspected of having cancer", as used herein, means a sample of individual, or tissue that already has or is predicted to have cancer or tumor.

The term "sample", as used herein, includes samples displaying a difference in expression level of TMAP/CKAP2 in cancer tissues of an individual, such as whole blood, serum, blood, plasma, saliva, urine, sputum, lymphatic fluid, cerebrospinal fluid, and interstitial fluid, and it includes any sample without limitation, as long as cell division can be detected therein.

In the method for providing information for diagnosing cancer prognosis of the present invention, antigen-antibody reaction levels are compared after treatment of the control group and the experimental group with the anti-TMAP/CKAP2 antibody. In the present invention, the antigen-antibody reaction level means an amount of binding products of TMAP/CKAP2 antigen and the antigen-recognizing antibody or the antigen-binding site thereof in the sample, and is an amount of antigen-antibody complexes. The antigen-antibody reaction level can be prepared, by a method typically used in the art without limitation. Examples of the method of determining the antigen-antibody reaction level may include Western blotting, ELISA (enzyme linked immunosorbent assay), RIA (radioimmunoassay), radioimmunodiffusion, ouchterlony immunodiffusion, rocket immunoelectrophoresis, immunohistostaining, immunoprecipitation assay, complement fixation assay, FACS, agglutination, and protein chip, but are not limited thereto.

ELISA, one of the representative methods of determining the antigen-antibody reaction level, is a simple and cost-effective method that allows for quantification of a large number of samples, and is widely used at present. In particular, this method is very sensitive, like RIA (radioimmunoassay). However, no radioactive isotopes are used in ELISA, unlike RIA. Thus, its use is increasing because of this advantage.

Agglutination means mass formation of particles resulting from, binding of antigen and antibody. In general, agglutination means tangled binding of antibodies and particle-type antigens insoluble in water such as cells. This reaction is visible, because antibodies function as an agglutinin and act as a bridge to link with antigens (agglutinogen).

Another method of analyzing the antigen-antibody reaction level is RIA (radioimmunoassay). This method is based on the immunoprecipitation of radioisotope-labeled standard antigen and antibody. In this regard, when non-radioisotope-labeled antigen (sample) is added, precipitation of radioisotope-labeled standard antigen is reduced to lower radioactivity in the precipitation, thereby determining the amount of antigen in the sample.

Meanwhile, the immunohistochemistry or immunohistochemical staining method includes an immunofluorescence method and an immunoenzyme method. The immunofluorescence method includes direct and indirect methods, and the immunoenzyme method includes direct and indirect methods, PAP method, ABC method, and LSAB method. The immunohistochemical staining method is a staining method for identifying the presence of tissue-specific antigen based on affinity of antibody to antigen. The immunohistochemical staining method is used to identify the origin of undifferentiated cells, the presence and absence of enzymes, hormones, tumor markers, and prognostic markers, the distinction between, carcinoma and sarcoma, and the distinction between benign and malignant tumors, and the primary site of metastatic cancer. In order to determine the antigen-antibody reaction level, the above methods can be applied to the method for providing information for diagnosing cancer prognosis of the present invention. Preferably, the present inventors identified intracellular TMAP/CKAP2 expression level and location via immunohistochemistry.

Further, various detection labels can be used to determine the antigen-antibody reaction level of the present invention. For example, the detection label may be selected from the group consisting of enzymes, fluorescent substances, ligands, luminescent substances, microparticles, and radioactive isotopes, but is not limited, thereto.

Examples of the enzyme available as a detection label include acetylcholinesterase, alkaline phosphatase, _-D-galactosidese, horseradish peroxidase, and _-lactase, and examples of the ligand include biotin derivatives. Examples of the luminescent substances include acridinium esters and isoluminol derivatives. Examples of the microparticle include colloidal gold and colored, latex. Examples of the radioactive isotopes include $^{37}Co$, $^{3}H$, $^{125}I$, $^{125}I$-Bolton-Hunter reagent.

In the present invention, the antigen-antibody reaction level is measured by using the above method so as to determine cancer occurrence in an individual suspected of having cancer, and furthermore to predict and diagnose the prognosis of cancer patients. Specifically, TMAP/CKAP2 expression of the present invention is increased in cancer cells in the metaphase and the anaphase of mitotic phase. When the antigen-antibody reaction level is increased in actively dividing cells of an individual suspected of having cancer, compared to the control sample, the corresponding individual can be determined, as a cancer patient and the patient with a history of cancer can be predicted to have a poor prognosis due to active proliferation. Preferably, this expression pattern becomes clearer in the patients suspected of having hepatic cancer or lung cancer, and much clearer in the patients suspected of having small cell, lung cancer. Therefore, diagnosis of these cancers can be more easily made. Also, it is possible to perform, accurate diagnosis and prognosis of breast, cancer and GIST, of which prognosis is closely associated with proliferation of cancer cells. Most preferably, the disease-free survival and the overall survival of breast cancer patients can be predicted with accuracy. The disease-free survival and the overall survival, can be clearly predicted by the TMAP/CKAP2 of the present, invention, as compared to Ki-67 known, as a marker of cell proliferation. Therefore, it is possible to provide clinical information for determining therapies of breast cancer patients.

In still another aspect, the present invention relates to a method, for screening a cancer therapeutic agent, comprising the steps of (a) determining the TMAP/CKAP2 antigen-antibody reaction level in cancer cells using the composition comprising the anti-TMAP/CKAP2 antibody or the antigen-binding site thereof; (b) treating the cells with a candidate substance; and (c) examining whether the antigen-antibody reaction level after treatment of the candidate substance of step (b) is lower than that of step (a).

The step of determining the expression level of TMAP/CKAP2 may be performed by using a typical analysis method known in the art without limitation, as described above, and examples thereof include Western blotting, ELISA, radioimmunoassay, radioimmunodiffusion, ouchterlony immunodiffusion, rocket immunoelectrophoresis, immunohistostaining, immunoprecipitation assay, complement fixation assay, FACS, and protein chip assay.

The term "candidate substance", as used herein, is a substance that is expected to treat cancer or to improve its prognosis, and any substance can be used without limitation, as long as it is expected to directly or indirectly ameliorate or improve cancer. Examples of the candidate substance include all therapeutic candidates such as compounds, genes and proteins. In the screening method of the present invention, expression levels of TMAP/CKAP2 are examined, before and after treatment of the candidate substances. When the expression level is reduced compared to before treatment of the candidate substance, the corresponding candidate substance can be determined as a putative therapeutic agent for cancer.

In still another aspect, the present invention relates to a composition for determining cell-division cycles, comprising the anti-TMAP/CKAP2 antibody or the antigen-binding site thereof.

In fact, many proteins, enzymes, and kinases are, not found in other phases, expressed during the mitotic phase, but all of them cannot be used as a specific marker for cell division. Until now, many researchers have made efforts to develop effective markers.

The antibody of the present invention is able to specifically bind with TMAP/CKAP2 that is expressed in the mitotic phase where cell division actively occurs, and its expression reaches a maximum level in the G2/M phases. Even though TMAP/CKAP2 is reported, to be expressed, in the mitotic phase, there are no reports whether it can be used, as a marker for mitosis through, immunohistochemistry. The present inventors confirmed that cells having a high expression level of TMAP/CKAP2 showed rapid cell division and growth rates, and cells having a low expression level of TMAP/CKAP2 showed low cell division and growth rates.

Currently, Ki-67 has been used as a marker for measuring cell mitosis and proliferation, and mainly found in nucleus. Thus, Ki-67 is disadvantageous in that it cannot be detected in cells in the mitotic phase because the nucleus disappears during the mitosis, and a ratio (%) of the cells stained by Ki-67 is too high to be used, as an index. For this reason, Ki-67 has a limit as a detection marker. In contrast, when the composition of the present invention is used, it specifically binds with spindle fibers regardless of the presence or absence of nucleus, thereby visualizing the cells in mitosis, and it shows specificity between cells before entering the mitotic phase and in mitosis, thereby detecting cells before and during proliferation at once. More particularly, the present inventors first demonstrated, that the composition of the present invention was used to detect, specific cell division phase. In order to confirm this, they treated cells with the antibody of the present invention. The result showed specific staining of the chromosome and spindle fibers of cells in mitosis.

More preferably, the composition of the present, invention is able to bind with the expressed TMAP/CKAP2 regardless of TMAP/CKAP2 phosphorylation, and thus detection can be continued, throughout the metaphase and anaphase in mitosis, not any point during mitosis. That is, if the possibility of protein detection varies according to phosphorylation involved in TMAP/CKAP2 activation, the detection is possible at any point during mitosis, and thus the entire expression level of TMAP/CKAP2 regardless of phosphorylation cannot, be detected. In contrast, the composition of the present invention is able to detect the expression level regardless of the protein phosphorylation, and thus it is possible to detect cell division, with accuracy.

In still another aspect, the present invention relates to use of the anti-TMAP/CKAP2 antibody or the antigen-binding site thereof in diagnosing the prognosis of cancer. Descriptions of the anti-TMAP/CKAP2 antibody or the antigen-binding site thereof, cancer, and diagnosing the prognosis are the same as described above.

In still another aspect, the present invention relates to use of the anti-TMAP/CKAP2 antibody or the antigen-binding site thereof in the determination of cell division cycle. Descriptions of the anti-TMAP/CKAP2 antibody or the antigen-binding site thereof, and cell division cycle are the same as described above.

Hereinafter, the present invention will be described in detail with reference to Examples. However, these Examples are for illustrative purposes only, and the invention, is not intended to be limited, by these Examples.

EXAMPLE 1

Monoclonal Antibody-Producing Hybridoma

In order to prepare human. TMAP/CKAP2 monoclonal antibody, mouse (m) TMAP/CKAP2 was first amplified and cloned into a pET-28a (+) vector which is an expression vector designed to express His tag at the N-terminus. After overexpression in bacteria, His-bind affinity chromatography, gel filtration chromatography, and SDS-PAGE gel elation were performed, to purify a single band on SDS-PAGE. Balb/c mouse was immunized with a recombinant His-TMAP/CKAP2 fusion protein obtained by the above method three times to obtain the spleen. After fusion of the spleen and SP2 myeloma cells, screening was performed using an ELISA plate coated with His-hTMAP/CKAP2 to obtain positive clones.

EXAMPLE 2

Amino Acid and DNA Sequencing of Anti-Human TMAP/CKAP2 Antibody by PCR

Total RNA was isolated from monoclonal antibody-producing hybridoma cells prepared in Example 1, and cDNA was synthesized therefrom, and subsequently, PCR was performed using an immunoglobulin-specific primer set, followed by sequencing.

In detail, for immunoglobulin PCR analysis, total RNA was isolated from, human TMAP/CKAP2 monoclonal antibody-producing hybridoma cells using a TRIzol reagent (Invitrogen, catalog number; 15596). cDNA synthesis was performed using a Superscript III First-strand Synthesis System for RT-PCR (Invitrogen, catalog number: 18080-051) according to manufacturer's recommendations. Each 5_g of the isolated total RNA was used for cDNA synthesis, cDNA synthesis was performed using primers of immunoglobulin 3'-conserved region sequence instead of oligo-d(T) primer. The primers of immunoglobulin 3'-conserved region sequence were used according to the sub-type of antibodies produced by each hybridoma cell. That is, if the sub-type of heavy chain of the produced antibody was immunoglobulin-M, MuIgMVH3'-1 was used, and if the sub-type was immunoglobulin-G, MuIgGVH3'-2 was used. In addition, if the sub-type of its light chain was a kappa (k)-chain, MuIgkVL3'-1 was used, and if the sub-type was lambda (_)-chain, MuIg_VL3'-1 was used. The used MuIgMVH3'-1, MuIgGVH3'-2, MuIgkVL3'-1, and MuIg_VL3'-1 primers were based, on mouse Ig-Primer Set (Novagen, catalog number 69831-3), and sequence information for each, primer is shown in Table 1.

TABLE 1

| SEQ ID-NO | Name | Bases | Degeneracy | aa position* | Sequence (5'-3') |
|---|---|---|---|---|---|
| 1 | MuIgV$_H$5'-A | 33 | 512 | −20 to −13 | GGGAATTCATGRASTTSKGGYTMARCTKGRTTT |
| 2 | MuIgV$_H$5'-B | 34 | 64 | −20 to −13 | GGGAATTCATGRAATGSASCTGGGTYWTYCTCTT |
| 3 | MuIgV$_H$5'-C | 39 | — | −20 to −11 | ACTAGTCGACATGGACTCCAGGCTCAATTTAGTTTTCCT |
| 4 | | 36 | 48 | −20 to −12 | ACTAGTCGACATGGCTGTCYTRGBGCTGYTCYTCTG |
| 5 | | 39 | 24 | −20 to −11 | ACTAGTCGACATGGVTTGGSTGTGGAMCTTGCYATTCCT |
| 6 | MnIgV$_H$5'-D | 36 | 8 | −20 to −12 | ACTAGTCGACATGAAATGCAGCTGGRTYATSTTCTT |
| 7 | | 36 | 32 | −20 to −12 | ACTAGTCGACATGGRCAGRCITACWTYYTCATTCCT |
| 8 | | 36 | — | −20 to −12 | ACTAGTCGACATGATGGTGTTAAGTCTTCTGTACCT |
| 9 | MuIgV$_H$5'-E | 36 | 8 | −20 to −12 | ACTAGTCGACATGGGATGGAGCTRTATCATSYTCTT |
| 10 | | 33 | 24 | −20 to −13 | ACTAGTCGACATGAAGWTGTGGBTRAACTGGRT |
| 11 | | 35 | 64 | −20 to −13 | ACTAGTCGACATGGRATGGASCKKIRTCTTTMTCT |
| 12 | MuIgV$_H$5'-F | 35 | 32 | −20 to −13 | ACTAGTCGACATGAACTTYGGGYTSAGMTTGRTTT |
| 13 | | 35 | — | −20 to −13 | ACTAGTCGACATGTACTTGGGACTGAGCTGTGTAT |
| 14 | | 33 | — | −20 to −13 | ACTAGTCGACATGAGAGTGCTGATTCTTTTGTG |
| 15 | | 38 | — | −20 to −12 | ACTAGTCGACATGGATTTTGGGCTGATTTTTTTATTG |
| 16 | MuIgMV$_H$3'-I | 32 | — | 125 to 118 | CCCAAGCTTACGAGGGGAAGACATTTGGGAA |
| 17 | MnIgGV$_H$3'-2 | 35 | 32 | 126 to 119 | CCCAAGCTTCCAGGGRCCARKGGATARACIGRTGG |
| 18 | MuIgkV$_L$5'-A | 32 | 32 | −20 to −13 | GGGAATTCATGRAGWCACAKWCYCAGGTCTTT |
| 19 | MuIgкV$_L$5'-B | 33 | — | −20 to −13 | GGGAATTCATGGAGACAGACACACTCCTGCTAT |
| 20 | MuIgкV$_L$5'-C | 39 | 8 | −20 to −11 | ACTAGTCGACATGGAGWCAGACACACTSCTGYTATGGGT |
| 21 | MuIgкV$_L$5'-D | 42 | 16 | −20 to −10 | ACTAGTCGACATGAGGRCCCCTGCTCAGWTTYTTGGIWTCTT |

TABLE 1-continued

| SEQ ID-NO | Name | Bases | Degeneracy | aa position* | Sequence (5'-3') |
|---|---|---|---|---|---|
| 22 | | 41 | 128 | −24 to −14 | ACTAGTCGAC ATG GGCWTCAAGATGRAGTCACAKWYYCWGG |
| 23 | MuIgκV$_L$5'-E | 39 | 4 | −20 to −11 | ACTAGTCGAC ATG AGTGTGCYCACTCAGGTCCTGGSGTT |
| 24 | | 41 | 32 | −15 to −5 | ACTAGTCGAC ATG TGGGGAYCGKTTTYAMMCTTTTCAATTG |
| 25 | | 38 | — | −20 to −11 | ACTAGTCGAC ATG GAAGCCCCAGCTCAGCTTCTCTTCC |
| 26 | MuIgκV$_L$5'-F | 36 | 32 | −20 to −12 | ACTAGTCGAC ATG AGIMMKTCIMTTCAITTCYTGGG |
| 27 | | 36 | 96 | −20 to −12 | ACTAGTCGAC ATG AKGTHCYCIGCTCAGYTYCTIRG |
| 28 | | 35 | 8 | −20 to −12 | ACTAGTCGAC ATG GTRTCCWCASCTCAGTTCCTTG |
| 29 | | 37 | — | −16 to −8 | ACTAGTCGAC ATG TATATATGTTTGTTGTCTATTTCT |
| 30 | MuIgκV$_L$5'-G | 39 | — | −19 to −10 | ACTAGTCGAC ATG AAGTTGCCTGTTAGGCTGTTGGTGCT |
| 31 | | 39 | 8 | −22 to −13 | ACTAGTCGAC ATG GATTTWCARGTGCAGATTWTCAGCTT |
| 32 | | 37 | 12 | −15 to −7 | ACTAGTCGAC ATG GTYCTYATVTCCTTGCTGTTCTGG |
| 33 | | 37 | 24 | −15 to −7 | ACTAGTCGAC ATG GTYCTYATVTTRCTGCTGCTATGG |
| 34 | MuIgκV$_L$3'-I | 30 | — | 122 to 116 | CCCAAGCTTACTGGATGGTGGGAAGAT GGA |
| 35 | MuIgλV$_L$5'-A | 33 | 128 | −20 to −13 | GGGAATTC ATG GCCTGGAYTYCWCTYWTMYTCT |
| 36 | MuIgλV$_L$3'-I | 32 | 32 | 125 to 118 | CCCAAGCTTAGCTCYTCWGWGGAIGGYGG RAA |

*Amino acid position of the primer relative to the start codon of the Ig variable region coding sequence.

The immunoglobulin-PCR reaction was performed, from cDNAs sequentially synthesized from anti-human TMAP/CKAP2 monoclonal antibody-producing hybridoma cells using mouse Ig-Primer Set (Novagen, catalog number 69831-3) and 2×PCR pre-Mix (SolGent, catalog number: STD01-M50h). PCR was performed according to recommendations of manufacturer of mouse Ig-Primer Set (Novagen, catalog number 69831-3), and each PCR of heavy chain and light chain was performed using 5'-primers having different, constructions.

That is, if the heavy chain is immunoglobulin-G or M, MuIgVH5'-A, MuIgVH5'-B, MuIgVH5'-C, MuIgVH5'-D, MuIgVH5'-E, and MuIgVH5'-F were used as the 5'-primer, and if the light chain is a kappa (k)-chain, MuIgkVL5'-A, MuIgkVL5'-B, MuIgkVL5'-G, MuIgkVL5'-D, MuIgkVL5'-E, MuIgkVL5'-F, and MuIgkVL5'-G were used, as the 5'-primer, and if the light chain is a lambda (_)-chain, MuIg_VL5'-A was used as the 5'-primer. Sequence information for each primer is shown in the above Table 1.

When A and E primers were used as the 5'-primer, PCR was performed, under the conditions of 94° C., 3-min→94° C., 1-min/50° C., 1-min/72° C., 2-min (35-cycles)→72° C., 6-min→4° C., and when C, D, E, F, and G primers were used as the 5'-primer, PCR was performed under the conditions of 94° C., 3-min→94° C., 1-min/60° C., 1-min/72° C., 2-min (35-cycles)→72° C., 6-min→4° C. The resulting PCR solution was separated by electrophoresis on 2% agarose gel (FIG. 1).

PCR bands were cut from the gel under UV light, and DMA extraction was performed according to a gel elution method, and used, for sequencing analysis.

The results are shown in FIGS. 2 and 3.

EXAMPLE 3

Immunohistochemistry of Hepatic Cancer, Lung Cancer, Cervical Cancer, Gastric Cancer, Colon Cancer, Breast Cancer, and Lung Cancer Tissues Using Anti-TMAP/CKAP2 Antibody or Anti-Ki-67 Antibody Immunohistochemistry was performed using a Ultravision LP Detection kit and DAB (Lab Vision Corporational Fremont, Calif., USA). A variety of human normal tissues and cancer tissue arrays were purchased from SuperBioChips. Tissue sections were deparaffinized in xylene, and heated in a 1 mM EDTA-containing 10 mM Tris buffer at pH 9.0 and 121° C. for 15 minutes for antigen retrieval. After fixation in 95% ethanol, the sections were reacted with primary antibody (culture dilution of anti-TMAP/CKAP2 monoclonal antibody or anti-Ki-67 monoclonal antibody-producing hybridoma) in a 20% FBS-supplemented TBST (Tris buffered saline with 0.05% Tween) solution at room temperature for 1 hour. The sections were washed with TBST, and then developed with DAB, followed by counterstaining with Mayer's Hematoxylin (DacoCytomation Denmark).

The results are shown in FIGS. 4 to 10.

EXAMPLE 4

Preparation of Breast Cancer Patients and Clinical Pathological Characterization Experiments were performed for 1.12 patients of invasive breast cancer who were diagnosed with invasive breast, cancer from 1999 to 2003 and with surgical treatment. The patients survived for at least 7 years. The detailed pathological characteristics of the patients are shown in the following Table 2. Most of the patients were patients with invasive ductal, carcinoma (84.8%) and luminal A type (45.5%).

TABLE 2

| variable | value (n = 112) |
|---|---|
| sex | |
| male | 3 |
| female | 109 |
| age at diagnosis (median, year) | 45 (range: 25-79) |
| tumor size (median, year) | 2.50 (range: 0.7-10) |
| histology | |
| invasive ductal carcinoma | 95 |
| mucinous carcinoma | 8 |
| other | 9 |
| T stage | |
| 1 | 49 |
| 2 | 51 |
| 3 | 12 |
| N stage | |
| 0 | 54 |
| 1 | 25 |
| 2 | 23 |
| 3 | 6 |
| n/a | 4 |
| ER | |
| negative | 50 |
| positive | 59 |
| n/a | 3 |
| PR | |
| negative | 52 |
| positive | 57 |
| n/a | 3 |
| HER2 | |
| negative | 75 |
| positive | 31 |
| n/a | 6 |
| p53 | |
| negative | 72 |
| positive | 36 |
| n/a | 4 |
| sub-type | |
| luminal A | 51 |
| luminal B | 12 |
| HER2 | 19 |
| triple negative | 24 |
| n/a | 6 |
| recurrence | |
| distant metastasis | 17 |
| local metastasis | 3 |
| local recurrence | 1 |

TABLE 2-continued

| variable | value (n = 112) |
|---|---|
| death | |
| death | 23 |
| survival | 87 |
| n/a | 2 |

EXAMPLE 5

Quantification of TMAP/CKAP2-Positive Cells in Breast Cancer Tissue and Evaluation of TMAP/CKAP2 Expression An average number of chromosomal TMAP/CKAP2-positive cells was counted at 200 magnification. The total number of cancer cells at 200 magnification was calculated based on 4-fold of the number of cells counted, at 400 magnification. The counting of the cells at 400 magnification was performed by comparison of 400 magnification images of 150, 200, 300, 350, 450, 500, 550, 900, and 1000 cancer cells. This method increases the counting efficiency even more. It is hard, to count cancer cells by simple comparison. When, irregular, all cancer cells in the microscopic field used, for the counting of TMAP/CKAP2 positive cells counted. When there were two specific areas in the cancer tissue, that is, different staining levels of chromosomal TMAP/CKAP2, a higher positive area, if more than 20% of the area, were occupied by cancer cells, was used, for counting cancer cells. The TMAP/CKAP2 expression levels were determined by the following four analysis methods.

1) Chromosome Permillage Analysis

A permillage of chromosomal TMAP/CKAP2 positive cells is a value (A/B) obtained from dividing the number of chromosomal TMAP/CKAP2 positive cells (A) by the total number of cancer cells in the area that, is used for counting the number of TMAP/CKAP2 positive cells (B). This analysis method was also used for examination of the TMAP/CKAP2 expression level, and other three analysis methods were used for examination of a correlation between TMAP/CKAP2 expression and overall, survival of patients.

2) Total Permillage Analysis

The cytoplasm as well as the chromosome was also stained with TMAP/CKAP2 antibodies. When the cytoplasmic staining was only observed, it was determined that the cells were in the G2 phase or the early M phase. Therefore, in order to include these positive cells in the proliferating cells, the number of cytoplasmic positive cells (A) was multiplied by 0.1, and added to the number of chromosomal positive cells (B), and then divided by the total number of cancer cells (C), which was defined as a total permillage [(A*0.1+B)/C].

3) Field Chromosome Count Analysis

The average number of chromosomal TMAP/CKAP2-positive cells at 200 magnification was defined as a field chromosome count.

4) Field Total Count Analysis

In order to consider the number of cytoplasmic-stained cells, the number of cytoplasmic-stained cells at 200 magnification (A) was multiplied by 0.1, and added, to the number of chromosomal positive cells (B), which was defined as the total number of TMAP/CKAP2-positive cells (A*0.1 B).

The above four different analysis methods were used to determine the TMAP/CKAP2 expression.

EXAMPLE 6

Analysis on Correlation Between TMAP/CKAP2 or Ki-67 Expression and Pathological Variations A correlation between TMAP/CKAP2 or Ki-67 expression and pathological variations was analyzed, by a Spearman's rank correlation test or a Wilcoxon rank sum test.

As shown in the following Table 3, there were correlations between TMAP/CKAP2 expression and pathological variables such as histological grade, nuclear grade, T stage, N stage, and ER and PR status, and also statistically significant correlations between Ki-67 expression and histological grade, nuclear grade, and ER and PR status.

TABLE 3

|  |  | histological grade | nuclear grade | T stage | N stage | ER | PR | HER2 |
|---|---|---|---|---|---|---|---|---|
| Field chromosome count | p or Z | 0.435 | 0.500 | 0.286 | 0.289 | −3.497 | −4.399 | −2.032 |
|  | *p | <0.001 | <0.001 | 0.002 | 0.003 | <0.001 | <0.001 | 0.042 |
| Field total count | p or Z | 0.388 | 0.461 | 0.317 | 0.258 | −3.338 | −4.021 | −2.276 |
|  | *p | <0.001 | <0.001 | 0.001 | 0.007 | 0.001 | <0.001 | 0.023 |
| Chromosome permillage | p or Z | 0.369 | 0.520 | 0.285 | 0.261 | −4.205 | −4.500 | −2.094 |
|  | *p | <0.001 | <0.001 | 0.002 | 0.006 | <0.001 | <0.001 | 0.036 |
| Total permillage | p or Z | 0.324 | 0.487 | 0.323 | 0.224 | −4.020 | −4.068 | −2.287 |
|  | *p | 0.001 | <0.001 | 0.001 | 0.020 | <0.001 | <0.001 | 0.022 |
| Ki-67 | p or Z | 0.385 | 0.551 | 0.069 | 0.400 | −3.514 | −2.788 | −1.890 |
|  | *p | <0.001 | <0.001 | 0.523 | 0.710 | <0.001 | 0.005 | 0.059 |

The following Table 4 showed that there was a close correlation between chromosome permillage and Ki-67 expression. Other analysis methods also showed that there were close correlations between TMAP/CKAP2 expression and pathological variables.

TABLE 4

|  | Field chromosome count | Field total count | Chromosome permillage | Total permillage |
|---|---|---|---|---|
| Field chromosome count | 1 | 0.965 | 0.940 | 0.895 |
| Field total count | 0.965 | 1 | 0.919 | 0.929 |
| Chromosome permillage | 0.940 | 0.919 | 1 | 0.973 |
| Total permillage | 0.895 | 0.929 | 0.972 | 1 |
| Ki-67 | 0.499 | 0.482 | 0.552 | 0.539 |

EXAMPLE 7

Analysis on Correlation Between Overall Survival (OS) or Disease Free Survival (DFS) and TMAP/CKAP2 or Ki-67 Expression in Breast Cancer Patient In accordance with the chromosomal permillage analysis method of TMAP/CKAP2 positive cells, patients showing different TMAP/CKAP2 or Ki-67 expression levels were divided into four groups for analysis; from Group 1 (low expression) to Group 4 (high expression).

The results of analyzing differences in overall survival and disease-free survival by Kaplan-Meier plot showed that Group 3 and Group 4 showed high chromosome permillage in TMAP/CKAP2 expression, and lower overall survival (OS; FIG. 11A) and disease-free survival (DFS; FIG. 11B) than Group 1.

There were significant, correlations between overall survival of patient and all variables such as age, nuclear grade, T stage, and N stage (Table 5). Recurrence information on breast cancer was incomplete, and only 20 cases were available for the study of recurrence time, and most of them were associated with death (16 deaths). Distant metastases were observed in 17 cases (85%), and local metastasis was observed in 1 case (5%). Both distant and local metastases were observed in 2 cases (10%). Metastases were frequently observed in the lung, bone, liver and brain. All 23 patients were associated with, breast cancer.

TABLE 5

|  | univariate analysis | | | multivariate analysis | | |
|---|---|---|---|---|---|---|
|  | hazard ratio | 95% CI | P | hazard ratio | 95% CI | P |
| age | 1.034 | 1.002 to 1.067 | 0.040 | 1.044 | 0.998 to 1.093 | 0.064 |
| Ki-67 |  |  | 0.082 |  |  |  |
| Group 1 and 2 (n42) | 1 |  |  |  |  |  |
| Group 3 (n20) | 4.047 | 1.184 to 13.832 | 0.026 |  |  |  |
| Group 4 (n25) | 2.701 | 0.762 to 9.575 | 0.124 |  |  |  |
| Chromosome Permillage of TMAP/CKAP2 positive cells |  |  | 0.001 |  |  | 0.016 |
| Group 1 and 2 (n = 56 or 47) | 1 |  |  | 1 |  |  |
| Group 3 (n = 27 or 24) | 10.665 | 2.303 to 49.379 | 0.002 | 12.894 | 1.353 to 122.921 | 0.026 |
| Group 4 (n = 27 or 24) | 16.906 | 3.777 to 75.659 | <0.001 | 24.673 | 2.684 to 226.812 | 0.005 |

TABLE 5-continued

| | univariate analysis | | | multivariate analysis | | |
|---|---|---|---|---|---|---|
| | hazard ratio | 95% CI | P | hazard ratio | 95% CI | P |
| histology | | | | | | |
| invasive ductal carcinoma | 1 | | 0.386 | | | |
| mucinous carcinoma | 0.037 | 0.000 to 33.602 | 0.343 | | | |
| other | 0.037 | 0.000 to 22.798 | 0.315 | | | |
| histological grade | | | 0.676 | | | |
| well differentiated | 1 | | | | | |
| moderately differentiated | 2.158 | 0.252 to 18.475 | 0.483 | | | |
| poorly differentiated | 2.458 | 0.326 to 18.535 | 0.383 | | | |
| nuclear grade | | | 0.080 | | | |
| 1 | 1 | | | | | |
| 2 | 0.751 | 0.084 to 6.727 | 0.798 | 0.105 | 0.005 to 2.055 | 0.138 |
| 3 | 2.549 | 0.335 to 19.388 | 0.366 | 0.107 | 0.005 to 2.178 | 0.146 |
| IHC marker | | | | | | |
| ER | 0.556 | 0.244 to 1.268 | 0.163 | | | |
| PR | 0.626 | 0.274 to 1.428 | 0.266 | | | |
| HER2 | 2.178 | 0.955 to 4.969 | 0.064 | 1.048 | 0.326 to 3.371 | 0.937 |
| P53 | 1.387 | 0.600 to 3.205 | 0.444 | | | |
| sub-type | | | | | | |
| luminal A | 1 | | | | | |
| luminal B | 2.588 | 0.757 to 8.846 | 0.129 | | | |
| HER2 positive | 3.046 | 1.021 to 9.052 | 0.046 | | | |
| triple negative | 2.023 | 0.679 to 6.021 | 0.206 | | | |
| T stage | | | 0.027 | | | 0.534 |
| 1 | 1 | | | 1 | | |
| 2 | 2.963 | 1.056 to 8.314 | 0.039 | 2.109 | 0.560 to 7.948 | 0.270 |
| 3 | 5.237 | 1.514 to 18.110 | 0.009 | 1.642 | 0.306 to 8.801 | 0.563 |
| N stage | | | 0.009 | | | 0.034 |
| 0 | 1 | | | 1 | | |
| 1 | 2.775 | 0.846 to 9.094 | 0.092 | 1.524 | 0.331 to 7.008 | 0.588 |
| 2 | 5.437 | 1.820 to 16.247 | 0.002 | 4.846 | 1.124 to 20.895 | 0.034 |
| 3 | 7.399 | 1.768 to 30.976 | 0.006 | 11.156 | 1.656 to 75.149 | 0.013 |

In Table 5, patients showing different TMAP/CKAP2 expression levels were divided into four groups at the same ratio, and were analyzed in accordance with the chromosomal permillage analysis method. For statistical analysis. Group 1 and Group 2 were made into a single group, and then compared with Group 3 and Group 4, and they were analyzed by univariate analysis and multivariate analysis.

The results of univariate analysis showed that Group 3 and Group 4 showed lower overall survival than Group 1 and Group 2. The results of multivariate analysis considering patient's age at diagnosis, nuclear grade, HER, and T and N stages showed that there was a statistically significant correlation between chromosome permillage and overall survival (p=0.016). Group 3 and Group 4 showed hazard ratios of 12.9 and 24.7, respectively, which are similar to or better than those by the N stage (4.8 for Group 2 and 11.2 for Group 3) which have been known to be the most highly associated with overall survival. These results suggest that TMAP/CKAP2 of the present, invention is a good predictor for hazard, ratio, comparable to K stage.

The results of Kaplan-Meier plots showed that Groups 2, 3 and 4 showed, higher Ki-67 expression levels than Group 1, and as Ki-67 expression was higher, overall survival was lower (FIG. 11C).

The overall survival according to N stage which has been known as a good predictor for the prognosis of breast cancer was shown in accordance with Kaplan-Meier plot. The results suggested, that prediction of overall survival based on TMAP/CKAP2 expression level of the present invention can be more accurate than that based, on N stage (FIG. 11D).

The following Table 6 showed the results of analyzing TMAP/CKAP2 expression levels in accordance with field chromosome count, field total count, and total permillage analysis methods, in addition to chromosomal permillage analysis. There was a statistically significance between high TMAP/CKAP2 expression level and low overall survival. The Kaplan Meier plot also showed the correlation between high TMAP/CKAP2 expression level and low overall survival, as in the results of chromosomal permillage analysis (FIG. 12),

TABLE 6

| | univariate analysis | | | multivariate analysis | | |
|---|---|---|---|---|---|---|
| | hazard ratio | 95% CI | P | hazard ratio | 95% CI | P |
| Field chromosome count | | | <0.001 | | | 0.003 |
| Group 1 and 2 (n = 55 or 43) | 1 | | | | | |
| Group 3 (n = 25 or 24) | 2.289 | 0.572 to 9.152 | 0.242 | 2.242 | 0.359 to 14.007 | 0.388 |
| Group 4 (n = 29 or 24) | 8.478 | 2.786 to 25.799 | <0.001 | 10.189 | 2.344 to 44.299 | 0.002 |
| Field total count | | | 0.001 | | | 0.009 |
| Group 1 and 2 (n = 55 or 46) | | | | | | |
| Group 3 (n = 26 or 33) | 8.467 | 1.758 to 40.772 | 0.008 | 10.713 | 1.780 to 64.485 | 0.010 |
| Group 4 (n = 28 or 22) | 16.759 | 3.776 to 74.375 | <0.001 | 12.883 | 2.468 to 67.252 | 0.002 |
| Chromosome permillage | | | 0.001 | | | 0.016 |
| Group 1 and 2 (n = 56 or 47) | 1 | | | 1 | | |
| Group 3 (n = 27 or 24) | 10.665 | 2.303 to 49.379 | 0.002 | 12.894 | 1.353 to 122.921 | 0.026 |
| Group 4 (n = 27 or 21) | 16.906 | 3.777 to 75.659 | <0.001 | 24.673 | 2.684 to 226.812 | 0.005 |
| Total permillage | | | 0.001 | | | 0.005 |
| Group 1 and 2 (n = 56 or 47) | | | | | | |
| Group 3 (n = 27 or 24) | 10.568 | 2.282 to 48.934 | 0.003 | 11.691 | 2.179 to 62.733 | 0.004 |
| Group 4 (n = 27 or 21) | 17.091 | 3.819 to 76.488 | <0.001 | 18.535 | 3.090 to 111.189 | 0.001 |

Another result showed that there was a correlation between TMAP/CKAP2 expression and disease-free survival (DFS) (following Tables 7 and 8). In accordance with chromosomal permillage analysis method, patients showing different TMAP/CKAP2 expression levels were divided into four groups. For statistical analysis, Group 1 and Group 2 were made into a single group, and then compared with Group 3 and Group 4, and they were analyzed by univariate analysis and multivariate analysis.

As a result, significantly low disease-free survivals were observed in Group 3 and Group 4 that, showed higher chromosomal permillage of TMAP/CKAP2 positive cells than Group 1 and Group 2 (p=0.014 for Group 3, p=0.024 for Group 4).

However, it was difficult to obtain patient information regarding disease-free survival (DFS). Thus, if the patient had no recurrence until the final examination, it was regarded as no recurrence at that point. All causes of patient's death was breast cancer, and the time of recurrence was regarded as the time of death to estimate disease-free survival (DFS) because recurrence time could not be inferred. Therefore, it is less reliable than overall survival (OS).

In accordance with other analysis methods than chromosomal permillage analysis, TMAP/CKAP2 expression level and disease-free survival, were analyzed. The results (Table 8) snowed that there were significant correlations between TMAP/CKAP2 expression and disease-free survival, and hazard, ratios are also similar to the results of chromosomal permillage analysis.

TABLE 7

| | univariate analysis | | | multivariate analysis | | |
|---|---|---|---|---|---|---|
| | hazard ratio | 95% CI | P | hazard ratio | 95% CI | P |
| Ki-67 | | | 0.087 | | | |
| Group 1 and 2 | 1 | | | | | |
| Group 3 | 3.084 | 1.070 to 8.888 | 0.037 | | | |
| Group 4 | 2.665 | 0.895 to 7.935 | 0.078 | | | |
| Chromosome permillage of TMAP/CKAP2 positive cells | | | 0.001 | | | 0.042 |
| Group 1 and 2 | 1 | | | 1 | | |
| Group 3 | 9.258 | 2.610 to 32.838 | 0.001 | 6.908 | 1.482 to 32.192 | 0.014 |
| Group 4 | 9.747 | 2.747 to 34.582 | <0.001 | 6.387 | 1.282 to 31.829 | 0.024 |
| histology | | | 0.576 | | | |
| invasive ductal carcinoma | 1 | | | | | |
| mucinous carcinoma | 0.354 | 0.048 to 2.613 | 0.294 | | | |
| other | 0.000 | 0.000 | 0.975 | | | |
| histological grade | | | 0.787 | | | |
| well differentiated | 1 | | | | | |
| moderately differentiated | 1.238 | 0.240 to 6.387 | 0.799 | | | |
| poorly differentiated | 1.548 | 0.360 to 6.653 | 0.557 | | | |
| nuclear grade | | | 0.094 | | | |
| 1 | 1 | | | | | |
| 2 | 1.441 | 0.173 to 11.972 | 0.735 | 0.155 | 0.010 to 2.404 | 0.182 |
| 3 | 3.620 | 0.480 to 27.307 | 0.212 | 0.154 | 0.010 to 2.434 | 0.184 |
| IHC marker | | | | | | |
| ER | 0.577 | 0.270 to 1.233 | 0.156 | | | |
| PR | 0.739 | 0.346 to 1.579 | 0.434 | | | |
| HER2 | 2.204 | 1.022 to 4.754 | 0.044 | 1.407 | 0.547 to 3.622 | 0.478 |
| P53 | 1.865 | 0.871 to 3.992 | 0.109 | | | |
| sub-type | | | | | | |
| luminal A | 1 | | | | | |
| luminal B | 3.653 | 0.821 to 9.586 | 0.023 | | | |

TABLE 7-continued

|  | univariate analysis | | | multivariate analysis | | |
| --- | --- | --- | --- | --- | --- | --- |
|  | hazard ratio | 95% CI | P | hazard ratio | 95% CI | P |
| HER2 positive | 2.601 | 0.902 to 7.502 | 0.077 | | | |
| triple negative | 2.107 | 0.790 to 5.619 | 0.136 | | | |
| T stage | | | 0.007 | | | 0.335 |
| 1 | 1 | | | 1 | | |
| 2 | 2.911 | 1.057 to 8.014 | 0.039 | 1.756 | 0.432 to 7.144 | 0.432 |
| 3 | 6.436 | 2.035 to 20.355 | 0.002 | 3.201 | 0.633 to 16.192 | 0.160 |
| N stage | | | 0.001 | | | 0.015 |
| 0 | 1 | | | 1 | | |
| 1 | 3.155 | 1.040 to 10.352 | 0.050 | 1.642 | 0.386 to 6.989 | 0.502 |
| 2 | 7.375 | 2.550 to 21.327 | <0.001 | 4.642 | 1.165 to 18.500 | 0.030 |
| 3 | 9.374 | 2.515 to 34.947 | 0.001 | 7.370 | 1.453 to 37.377 | 0.016 |

TABLE 8

|  | univariate analysis | | | multivariate analysis | | |
| --- | --- | --- | --- | --- | --- | --- |
|  | hazard ratio | 95% CI | P | hazard ratio | 95% CI | P |
| Field chromosome count | | | <0.001 | | | 0.051 |
| Group 1 and 2 (n = 51 or 40) | 1 | | | | | |
| Group 3 (n = 54 or 22) | 1.849 | 0.564 to 6.060 | 0.310 | 1.721 | 0.409 to 7.231 | 0.459 |
| Group 4 (n = 28 or 24) | 6.206 | 2.470 to 16.030 | <0.001 | 3.814 | 1.247 to 11.665 | 0.019 |
| Field total count | | | 0.001 | | | 0.017 |
| Group 1 and 2 (n = 51 or 43) | | | | | | |
| Group 3 (n = 26 or 22) | 5.626 | 1.861 to 36.033 | 0.004 | 6.599 | 1.593 to 27.343 | 0.009 |
| Group 4 (n = 26 or 21) | 8.179 | 1.338 to 17.894 | <0.001 | 3.982 | 1.167 to 13.585 | 0.027 |
| Chromosome permillage | | | 0.001 | | | 0.042 |
| Group 1 and 2 (n = 51 or 42) | 1 | | | 1 | | |
| Group 3 (n = 26 or 24) | 9.258 | 2.610 to 32.838 | 0.001 | 6.908 | 1.482 to 32.192 | 0.014 |
| Group 4 (n = 27 or 21) | 9.747 | 2.747 to 34.582 | <0.001 | 6.387 | 1.282 to 31.829 | 0.024 |
| Total permillage | | | <0.001 | | | 0.028 |
| Group 1 and 2 (n = 52 or 43) | 1 | | | | | |
| Group 3 (n = 25 or 23) | 5.897 | 1.848 to 18.814 | 0.003 | 4.239 | 1.232 to 14.586 | 0.022 |
| Group 4 (n = 27 or 21) | 8.228 | 2.679 to 25.277 | <0.001 | 5.563 | 1.416 to 21.853 | 0.014 |

EXAMPLE 8

Analysis on correlation between overall survival (OS) and TMAP/CKAP2 Expression in 23 Deaths of Breast Cancer Patient The close correlation between TMAP/CKAP2 expression and prognostic variables such as N and T stages implies a correlation between TMAP/CKAP2 expression and early death.

In accordance with chromosome permillage analysis (FIG. 13A) and total permillage analysis (FIG. 13B), the correlation between TMAP/CKAP2 expression and overall-survival (OS) was analyzed, and the results were represented as Kaplan-Meier plot in FIG. 13.

The results showed that higher TMAP/CKAP2 expression showed, lower overall survival (OS), indicating that high-risk patients have high probability of death and aggressive treatment is recommended. Thus, it is clinically significant.

EXAMPLE 9

Comparison Between Ki-67 and TMAP/CKAP2 as Prognostic Marker

Currently, Ki-67 has been used as a marker for measuring cell mitosis and proliferation, and mainly found, in nucleus. Thus, Ki-67 is disadvantageous in that it cannot be detected in cells entering the mitotic phase because the nucleus disappears during the mitosis. Actually, a correlation between Ki-67 expression level, and overall survival of cancer patients has not been clarified yet.

As shown in FIG. 11C, the result of analyzing the correlation between Ki-67 expression level and overall survival showed that Ki-67 expression was less correlated, with overall, survival than TMAP/CKAP2 expression (FIGS. 11A and 11B). As shown in FIG. 11C, Group 1 showing the lowest Ki-67 expression snowed higher overall survival than other groups, but there were no significant differences between Groups 2, 3, and 4. In contrast, the result of FIG. 11A snowed that the correlations between TMAP/CKAP2 and overall survival were clearly observed in Groups 2, 3, and 4. These results imply that Ki-67 has not been a good, predictor.

From the viewpoint of biology, chromosomal TMAP/CKAP2 expression can be observed from late metaphase to immediately after cytokinesis, but Ki-67 is observed in the nucleus throughout the cell, cycle from late G1 phase. Thus, it can be seen that overall survival is more closely correlated, with mitotic phase. This result is consistent with the previous report, that direct counting of mitotic cells in H&E-stained sections under a microscope is better than the use of Ki-67.

Taken together, the results support that the TMAP/CKAP2 expression of the present invention can be used, as a powerful predictor of overall survival and disease-free survival of breast cancer patients.

Effect of the Invention

The antibody according to the present invention or the fragment thereof specifically binds to a phosphorylated or unphosphorylated form of TMAP/CKAP2 that, is expressed in the metaphase and the anaphase of mitotic phase, and thus can be used in the studies regarding cell cycles and TMAP/CKAP2 functions. It can be also used for the diagnosis of breast cancer or GIST of which prognosis is determined by mitotic activity and for the development of anticancer agents.

Further, disease-free survival and overall survival of breast cancer patients can be predicted, thereby providing important information for the prognosis of breast cancer, development of therapeutic agents, and selection of appropriate treatment.

What is claimed is:

1. A method for diagnosing breast cancer prognosis, comprising:
   (a) treating a control sample separated from an individual known to have a good breast cancer prognosis and a sample separated from a test individual suspected of having breast cancer with an anti-TMAP/CKAP2 antibody or an antigen-binding fragment thereof;
   (b) comparing antigen-antibody reaction levels of step (a); and
   (c) determining the individual suspected of having breast cancer as a cancer patient having a poor prognosis when the antigen-antibody reaction level of the sample separated from the test individual is higher than that of the control sample in step (b);
   wherein the antibody comprises a heavy chain variable region comprising heavy chain CDR1 represented by SEQ ID NO. 38; heavy chain CDR2 represented by SEQ ID NO. 39; and heavy chain CDR3 represented by SEQ ID NO. 40 and a light chain variable region comprising light chain CDR1 represented by SEQ ID NO. 42; light chain CDR2 represented by SEQ ID NO. 43; and light chain CDR3 represented by SEQ ID NO. 44; or a heavy chain amino acid sequence represented by SEQ ID NO. 45 and a light chain amino acid sequence represented by SEQ ID NO. 46.

2. The method according to claim 1, wherein the cancer prognosis is to predict the disease-free survival or overall survival of the individual.

3. The method according to claim 1, wherein the sample is any one or more of whole blood, serum, plasma, saliva, urine, sputum, lymphatic fluid, or cells isolated from an individual.

4. A method for detecting TMAP/CKAP2 in an individual having breast cancer, comprising:
   binding a composition comprising an anti-TMAP/CKAP2 (Tumor associated microtubule associated protein/cytoskeleton associated protein 2) antibody or an antigen-binding fragment thereof to TMAP/CKAP2 expressed in a cell from the individual, thereby detecting TMAP/CKAP2;

wherein the antibody comprises a heavy chain variable region comprising heavy chain CDR1 represented by SEQ ID NO. 38; heavy chain CDR2 represented by SEQ ID NO. 39; and heavy chain CDR3 represented by SEQ ID NO. 40 and a light chain variable region comprising light chain CDR1 represented by SEQ ID NO. 42; light chain CDR2 represented by SEQ ID NO. 43; and light chain CDR3 represented by SEQ ID NO. 44; or a heavy chain amino acid sequence represented by SEQ ID NO. 45 and a light chain amino acid sequence represented by SEQ ID NO. 46.

5. The method according to claim 4, wherein binding the composition detects mitosis of cells.

* * * * *

```
                        SEQUENCE LISTING

<160> NUMBER OF SEQ ID NOS: 46

<210> SEQ ID NO 1
<211> LENGTH: 33
<212> TYPE: DNA
<213> ORGANISM: Artificial Sequence
<220> FEATURE:
<223> OTHER INFORMATION: MuIgVH5'-A primer

<400> SEQUENCE: 1
gggaattcat grasttskgg ytmarctkgr ttt                              33

<210> SEQ ID NO 2
<211> LENGTH: 34
<212> TYPE: DNA
<213> ORGANISM: Artificial Sequence
<220> FEATURE:
<223> OTHER INFORMATION: MuIgVH5'-B primer

<400> SEQUENCE: 2
gggaattcat graatgsasc tgggtywtyc tctt                             34

<210> SEQ ID NO 3
<211> LENGTH: 39
<212> TYPE: DNA
<213> ORGANISM: Artificial Sequence
<220> FEATURE:
<223> OTHER INFORMATION: MuIgVH5'-C primer

<400> SEQUENCE: 3
actagtcgac atggactcca ggctcaattt agttttcct                        39

<210> SEQ ID NO 4
<211> LENGTH: 36
<212> TYPE: DNA
<213> ORGANISM: Artificial Sequence
<220> FEATURE:
<223> OTHER INFORMATION: MuIgVH5'-C primer

<400> SEQUENCE: 4
actagtcgac atggctgtcy trgbgctgyt cytctg                           36

<210> SEQ ID NO 5
<211> LENGTH: 39
<212> TYPE: DNA
<213> ORGANISM: Artificial Sequence
<220> FEATURE:
<223> OTHER INFORMATION: MuIgVH5'-C primer

<400> SEQUENCE: 5
actagtcgac atggvttggs tgtggamctt gcyattcct                        39

<210> SEQ ID NO 6
<211> LENGTH: 36
<212> TYPE: DNA
<213> ORGANISM: Artificial Sequence
<220> FEATURE:
<223> OTHER INFORMATION: MuIgVH5'-D primer

<400> SEQUENCE: 6
actagtcgac atgaaatgca gctggrtyat sttctt                           36
```

```
<210> SEQ ID NO 7
<211> LENGTH: 36
<212> TYPE: DNA
<213> ORGANISM: Artificial Sequence
<220> FEATURE:
<223> OTHER INFORMATION: MuIgVH5'-D primer

<400> SEQUENCE: 7
actagtcgac atggrcagrc ttacwtyytc attcct                              36

<210> SEQ ID NO 8
<211> LENGTH: 36
<212> TYPE: DNA
<213> ORGANISM: Artificial Sequence
<220> FEATURE:
<223> OTHER INFORMATION: MuIgVH5'-D primer

<400> SEQUENCE: 8
actagtcgac atgatggtgt taagtcttct gtacct                              36

<210> SEQ ID NO 9
<211> LENGTH: 36
<212> TYPE: DNA
<213> ORGANISM: Artificial Sequence
<220> FEATURE:
<223> OTHER INFORMATION: MuIgVH5'-E primer

<400> SEQUENCE: 9
actagtcgac atgggatgga gctrtatcat sytctt                              36

<210> SEQ ID NO 10
<211> LENGTH: 33
<212> TYPE: DNA
<213> ORGANISM: Artificial Sequence
<220> FEATURE:
<223> OTHER INFORMATION: MuIgVH5'-E primer

<400> SEQUENCE: 10
actagtcgac atgaagwtgt ggbtraactg grt                                 33

<210> SEQ ID NO 11
<211> LENGTH: 35
<212> TYPE: DNA
<213> ORGANISM: Artificial Sequence
<220> FEATURE:
<223> OTHER INFORMATION: MuIgVH5'-E primer
<220> FEATURE:
<221> NAME/KEY: modified_base
<222> LOCATION: (25)
<223> OTHER INFORMATION: n=inosine

<400> SEQUENCE: 11
actagtcgac atggratgga sckknrtctt tmtct                               35

<210> SEQ ID NO 12
<211> LENGTH: 35
<212> TYPE: DNA
<213> ORGANISM: Artificial Sequence
<220> FEATURE:
<223> OTHER INFORMATION: MuIgVH5'-F primer

<400> SEQUENCE: 12
actagtcgac atgaacttyg ggytsagmtt grttt                               35
```

```
<210> SEQ ID NO 13
<211> LENGTH: 35
<212> TYPE: DNA
<213> ORGANISM: Artificial Sequence
<220> FEATURE:
<223> OTHER INFORMATION: MuIgVH5'-F primer

<400> SEQUENCE: 13
actagtcgac atgtacttgg gactgagctg tgtat                               35

<210> SEQ ID NO 14
<211> LENGTH: 33
<212> TYPE: DNA
<213> ORGANISM: Artificial Sequence
<220> FEATURE:
<223> OTHER INFORMATION: MuIgVH5'-F primer

<400> SEQUENCE: 14
actagtcgac atgagagtgc tgattctttt gtg                                 33

<210> SEQ ID NO 15
<211> LENGTH: 38
<212> TYPE: DNA
<213> ORGANISM: Artificial Sequence
<220> FEATURE:
<223> OTHER INFORMATION: MuIgVH5'-F primer

<400> SEQUENCE: 15
actagtcgac atggattttg ggctgatttt ttttattg                            38

<210> SEQ ID NO 16
<211> LENGTH: 32
<212> TYPE: DNA
<213> ORGANISM: Artificial Sequence
<220> FEATURE:
<223> OTHER INFORMATION: MuIgMVH3'-1 primer

<400> SEQUENCE: 16
cccaagctta cgagggggaa gacatttggg aa                                  32

<210> SEQ ID NO 17
<211> LENGTH: 35
<212> TYPE: DNA
<213> ORGANISM: Artificial Sequence
<220> FEATURE:
<223> OTHER INFORMATION: MuIgGVH3'-2 primer
<220> FEATURE:
<221> NAME/KEY: modified_base
<222> LOCATION: (30)
<223> OTHER INFORMATION: n=inosine

<400> SEQUENCE: 17
cccaagcttc cagggrccar kggataracn grtgg                               35

<210> SEQ ID NO 18
<211> LENGTH: 32
<212> TYPE: DNA
<213> ORGANISM: Artificial Sequence
<220> FEATURE:
<223> OTHER INFORMATION: MuIgKappaVL5'-A primer

<400> SEQUENCE: 18
gggaattcat gragwcacak wcycaggtct tt                                  32
```

```
<210> SEQ ID NO 19
<211> LENGTH: 33
<212> TYPE: DNA
<213> ORGANISM: Artificial Sequence
<220> FEATURE:
<223> OTHER INFORMATION: MuIgKappaVL5'-B primer

<400> SEQUENCE: 19
gggaattcat ggagacagac acactcctgc tat                              33

<210> SEQ ID NO 20
<211> LENGTH: 39
<212> TYPE: DNA
<213> ORGANISM: Artificial Sequence
<220> FEATURE:
<223> OTHER INFORMATION: MuIgKappaVL5'-C primer

<400> SEQUENCE: 20
actagtcgac atggagwcag acacactsct gytatgggt                         39

<210> SEQ ID NO 21
<211> LENGTH: 42
<212> TYPE: DNA
<213> ORGANISM: Artificial Sequence
<220> FEATURE:
<223> OTHER INFORMATION: MuIgKappaVL5'-D primer
<220> FEATURE:
<221> NAME/KEY: modified_base
<222> LOCATION: (37)
<223> OTHER INFORMATION: n=inosine

<400> SEQUENCE: 21
actagtcgac atgaggrccc ctgctcagwt tyttggnwtc tt                     42

<210> SEQ ID NO 22
<211> LENGTH: 41
<212> TYPE: DNA
<213> ORGANISM: Artificial Sequence
<220> FEATURE:
<223> OTHER INFORMATION: MuIgKappaVL5'-D primer

<400> SEQUENCE: 22
actagtcgac atgggcwtca agatgragtc acakwyycwg g                      41

<210> SEQ ID NO 23
<211> LENGTH: 39
<212> TYPE: DNA
<213> ORGANISM: Artificial Sequence
<220> FEATURE:
<223> OTHER INFORMATION: MuIgKappaVL5'-E primer

<400> SEQUENCE: 23
actagtcgac atgagtgtgc ycactcaggt cctggsgtt                         39

<210> SEQ ID NO 24
<211> LENGTH: 41
<212> TYPE: DNA
<213> ORGANISM: Artificial Sequence
<220> FEATURE:
<223> OTHER INFORMATION: MuIgKappaVL5'-E primer

<400> SEQUENCE: 24
actagtcgac atgtggggay cgktttyamm cttttcaatt g                      41
```

```
<210> SEQ ID NO 25
<211> LENGTH: 38
<212> TYPE: DNA
<213> ORGANISM: Artificial Sequence
<220> FEATURE:
<223> OTHER INFORMATION: MuIgKappaVL5'-E primer

<400> SEQUENCE: 25
actagtcgac atggaagccc cagctcagct tctcttcc                              38

<210> SEQ ID NO 26
<211> LENGTH: 36
<212> TYPE: DNA
<213> ORGANISM: Artificial Sequence
<220> FEATURE:
<223> OTHER INFORMATION: MuIgKappaVL5'-F primer
<220> FEATURE:
<221> NAME/KEY: modified_base
<222> LOCATION: (16)
<223> OTHER INFORMATION: n=inosine
<220> FEATURE:
<221> NAME/KEY: modified_base
<222> LOCATION: (22)
<223> OTHER INFORMATION: n=inosine
<220> FEATURE:
<221> NAME/KEY: modified_base
<222> LOCATION: (28)
<223> OTHER INFORMATION: n=inosine

<400> SEQUENCE: 26
actagtcgac atgagnmmkt cnmttcantt cytggg                                36

<210> SEQ ID NO 27
<211> LENGTH: 36
<212> TYPE: DNA
<213> ORGANISM: Artificial Sequence
<220> FEATURE:
<223> OTHER INFORMATION: MuIgKappaVL5'-F primer
<220> FEATURE:
<221> NAME/KEY: modified_base
<222> LOCATION: (22)
<223> OTHER INFORMATION: n=inosine
<220> FEATURE:
<221> NAME/KEY: modified_base
<222> LOCATION: (34)
<223> OTHER INFORMATION: n=inosine

<400> SEQUENCE: 27
actagtcgac atgakgthcy cngctcagyt yctnrg                                36

<210> SEQ ID NO 28
<211> LENGTH: 35
<212> TYPE: DNA
<213> ORGANISM: Artificial Sequence
<220> FEATURE:
<223> OTHER INFORMATION: MuIgKappaVL5'-F primer

<400> SEQUENCE: 28
actagtcgac atggtrtccw casctcagtt ccttg                                 35

<210> SEQ ID NO 29
<211> LENGTH: 37
<212> TYPE: DNA
<213> ORGANISM: Artificial Sequence
<220> FEATURE:
<223> OTHER INFORMATION: MuIgKappaVL5'-F primer

<400> SEQUENCE: 29
actagtcgac atgtatatat gtttgttgtc tatttct                               37
```

<210> SEQ ID NO 30
<211> LENGTH: 39
<212> TYPE: DNA
<213> ORGANISM: Artificial Sequence
<220> FEATURE:
<223> OTHER INFORMATION: MuIgKappaVL5'-G primer

<400> SEQUENCE: 30
actagtcgac atgaagttgc ctgttaggct gttggtgct          39

<210> SEQ ID NO 31
<211> LENGTH: 39
<212> TYPE: DNA
<213> ORGANISM: Artificial Sequence
<220> FEATURE:
<223> OTHER INFORMATION: MuIgKappaVL5'-G primer

<400> SEQUENCE: 31
actagtcgac atggatttwc argtgcagat twtcagctt          39

<210> SEQ ID NO 32
<211> LENGTH: 37
<212> TYPE: DNA
<213> ORGANISM: Artificial Sequence
<220> FEATURE:
<223> OTHER INFORMATION: MuIgKappaVL5'-G primer

<400> SEQUENCE: 32
actagtcgac atggtyctya tvtccttgct gttctgg            37

<210> SEQ ID NO 33
<211> LENGTH: 37
<212> TYPE: DNA
<213> ORGANISM: Artificial Sequence
<220> FEATURE:
<223> OTHER INFORMATION: MuIgKappaVL5'-G primer

<400> SEQUENCE: 33
actagtcgac atggtyctya tvttrctgct gctatgg            37

<210> SEQ ID NO 34
<211> LENGTH: 30
<212> TYPE: DNA
<213> ORGANISM: Artificial Sequence
<220> FEATURE:
<223> OTHER INFORMATION: MuIgKappaVL3'-1 primer

<400> SEQUENCE: 34
cccaagctta ctggatggtg ggaagatgga                    30

<210> SEQ ID NO 35
<211> LENGTH: 33
<212> TYPE: DNA
<213> ORGANISM: Artificial Sequence
<220> FEATURE:
<223> OTHER INFORMATION: MuIgLamdaVL5'-A primer

<400> SEQUENCE: 35
gggaattcat ggcctggayt ycwctywtmy tct                33

<210> SEQ ID NO 36
<211> LENGTH: 32
<212> TYPE: DNA
<213> ORGANISM: Artificial Sequence
<220> FEATURE:
<223> OTHER INFORMATION: MuIgLamdaVL3'-1 primer

```
<220> FEATURE:
<221> NAME/KEY: modified_base
<222> LOCATION: (24)
<223> OTHER INFORMATION: n=inosine

<400> SEQUENCE: 36
cccaagctta gctcytcwgw gganggyggr aa                                      32

<210> SEQ ID NO 37
<211> LENGTH: 417
<212> TYPE: DNA
<213> ORGANISM: Artificial Sequence
<220> FEATURE:
<223> OTHER INFORMATION: human TMAP/CKAP2 Heavy G-C

<400> SEQUENCE: 37
ctagtcgaca tgggttgggt gtggaccttg ccattcctcc tgtcaggaac tgcaggtgtc        60
cattgccagg ctcagctgca gcagtctgga cctgagctgg tgaagcctgg gctttagtg       120 aagatatcct gcaaggcttc tggttatatc ttcacaaact acgatataaa ctgggtgaag      180
cagaggcctg gacagggtct tgagtggatt ggattgattt atcctggaga tggcagtatt      240
aagtacaatg agaaattcaa gggcaaggcc acactgactg cagacaaatc ctccagcaca      300
gcctacatgc agctcagcag ccagacttct gagaactctg cagtctattt ctgtgcaaga      360
tccggcccgt attactttga ctatctgggg ccaaggcacc actctcacag ttctcgc         417

<210> SEQ ID NO 38
<211> LENGTH: 5
<212> TYPE: PRT
<213> ORGANISM: Artificial Sequence
<220> FEATURE:
<223> OTHER INFORMATION: CDR1 of heavy chain

<400> SEQUENCE: 38

Asn Tyr Asp Ile Asn
1               5

<210> SEQ ID NO 39
<211> LENGTH: 19
<212> TYPE: PRT
<213> ORGANISM: Artificial Sequence
<220> FEATURE:
<223> OTHER INFORMATION: CDR2 of heavy chain

<400> SEQUENCE: 39

Leu Ile Tyr Pro Gly Asp Gly Ser Ile Lys Tyr Asn Glu Lys Phe Lys
1               5                   10                  15

Gly Lys Gly

<210> SEQ ID NO 40
<211> LENGTH: 9
<212> TYPE: PRT
<213> ORGANISM: Artificial Sequence
<220> FEATURE:
<223> OTHER INFORMATION: CDR3 of heavy chain

<400> SEQUENCE: 40

Ser Gly Pro Tyr Tyr Phe Asp Tyr Leu
1               5

<210> SEQ ID NO 41
<211> LENGTH: 400
<212> TYPE: DNA
<213> ORGANISM: Artificial Sequence
```

```
<220> FEATURE:
<223> OTHER INFORMATION: human TMAP/CKAP2 Light k-E k-F

<400> SEQUENCE: 41
actagtcgac atgagtgtgc ycactcaggt cctggggttg cttatgttct ggatctctgg      60
agtcagtggg gatattgtga taacccagga tgaactctcc aatcctgtca ttttggaga     120 atcagtttcc atctcctgca ggtctagtaa gagtctccta tataaggatg gaagacata     180 cttgaattgg tatctgcaga gaccaggaca atctcctcag ctcctgatct atttgatgtc     240
cacccgtgca tcaggagtct cagaccggtt tagtggcagt gggtcaggaa cagatttcac     300
cctggaaatc agtagagtga aggctgagga tgtgggtgtg tattactgcc aacaagttgt     360
agagtatcca ttcacgttcg gctcggggac aaaatggaaa                           400

<210> SEQ ID NO 42
<211> LENGTH: 16
<212> TYPE: PRT
<213> ORGANISM: Artificial Sequence
<220> FEATURE:
<223> OTHER INFORMATION: CDR1 of light chain

<400> SEQUENCE: 42

Arg Ser Ser Lys Ser Leu Leu Tyr Lys Asp Gly Lys Thr Tyr Leu Asn
1               5                   10                  15

<210> SEQ ID NO 43
<211> LENGTH: 7
<212> TYPE: PRT
<213> ORGANISM: Artificial Sequence
<220> FEATURE:
<223> OTHER INFORMATION: CDR2 of light chain

<400> SEQUENCE: 43

Leu Met Ser Thr Arg Ala Ser
1               5

<210> SEQ ID NO 44
<211> LENGTH: 9
<212> TYPE: PRT
<213> ORGANISM: Artificial Sequence
<220> FEATURE:
<223> OTHER INFORMATION: CDR3 of light chain

<400> SEQUENCE: 44

Gln Gln Val Val Glu Tyr Pro Phe Thr
1               5

<210> SEQ ID NO 45
<211> LENGTH: 139
<212> TYPE: PRT
<213> ORGANISM: Artificial Sequence
<220> FEATURE:
<223> OTHER INFORMATION: human TMAP/CKAP2 heavy chain

<400> SEQUENCE: 45

Leu Val Asp Met Gly Trp Val Trp Thr Leu Pro Phe Leu Leu Ser Gly
1               5                   10                  15

Thr Ala Gly Val His Cys Gln Ala Gln Leu Gln Gln Ser Gly Pro Glu
                20                  25                  30

Leu Val Lys Pro Gly Ala Leu Val Lys Ile Ser Cys Lys Ala Ser Gly
            35                  40                  45

Tyr Ile Phe Thr Asn Tyr Asp Ile Asn Trp Val Lys Gln Arg Pro Gly
        50                  55                  60
```

```
Gln Gly Leu Glu Trp Ile Gly Leu Ile Tyr Pro Gly Asp Gly Ser Ile
 65              70                  75                  80

Lys Tyr Asn Glu Lys Phe Lys Gly Lys Ala Thr Leu Thr Ala Asp Lys
                 85                  90                  95

Ser Ser Ser Thr Ala Tyr Met Gln Leu Ser Ser Gln Thr Ser Glu Asn
                100                 105                 110

Ser Ala Val Tyr Phe Cys Ala Arg Ser Gly Pro Tyr Tyr Phe Asp Tyr
            115                 120                 125

Leu Gly Pro Arg His His Ser His Ser Ser Arg
        130                 135

<210> SEQ ID NO 46
<211> LENGTH: 133
<212> TYPE: PRT
<213> ORGANISM: Artificial Sequence
<220> FEATURE:
<223> OTHER INFORMATION: human TMAP/CKAP2 light chain
<220> FEATURE:
<221> NAME/KEY: MISC_FEATURE
<222> LOCATION: (7)
<223> OTHER INFORMATION: XAA=any amino acid

<400> SEQUENCE: 46

Leu Val Asp Met Ser Val Xaa Thr Gln Val Leu Gly Leu Leu Met Phe
  1               5                  10                  15

Trp Ile Ser Gly Val Ser Gly Asp Ile Val Ile Thr Gln Asp Glu Leu
                 20                  25                  30

Ser Asn Pro Val Ile Phe Gly Glu Ser Val Ser Ile Ser Cys Arg Ser
                 35                  40                  45

Ser Lys Ser Leu Leu Tyr Lys Asp Gly Lys Thr Tyr Leu Asn Trp Tyr
 50                  55                  60

Leu Gln Arg Pro Gly Gln Ser Pro Gln Leu Leu Ile Tyr Leu Met Ser
 65                  70                  75                  80

Thr Arg Ala Ser Gly Val Ser Asp Arg Phe Ser Gly Ser Gly Ser Gly
                 85                  90                  95

Thr Asp Phe Thr Leu Glu Ile Ser Arg Val Lys Ala Glu Asp Val Gly
                100                 105                 110

Val Tyr Tyr Cys Gln Gln Val Val Glu Tyr Pro Phe Thr Phe Gly Ser
            115                 120                 125

Gly Thr Lys Trp Lys
        130
```